United States Patent [19]

Ackerman et al.

[11] Patent Number: 5,197,487
[45] Date of Patent: Mar. 30, 1993

[54] MEASURING PROBE

[75] Inventors: Jerome B. Ackerman, Woodmont, Conn.; Thomas T. Ackerman, Fairfield, Conn.; Mitchell N. Ackerman, Providence, R.I.; Herbert J. Hedberg, Attleboro, Mass.

[73] Assignee: Jerome B. Ackerman, New York, N.Y.

[21] Appl. No.: 627,887

[22] Filed: Dec. 13, 1990

Related U.S. Application Data

[63] Continuation of Ser. No. 24,991, Mar. 20, 1987, abandoned, which is a continuation-in-part of Ser. No. 846,180, Mar. 3, 1986, Pat. No. 4,665,621.

[51] Int. Cl.$^5$ .............................................. A61B 5/103
[52] U.S. Cl. ........................................ 128/776; 33/514
[58] Field of Search ...................... 128/774, 776–777; 433/32; 33/511, 513–514, 169 B, 172 E

[56] References Cited

U.S. PATENT DOCUMENTS

| | | | |
|---|---|---|---|
| 3,058,225 | 10/1962 | Ward | 128/776 X |
| 3,559,292 | 2/1971 | Weissman | 33/513 X |
| 3,943,914 | 3/1976 | Grenfell et al. | 33/514 X |
| 4,027,669 | 6/1977 | Johnston et al. | 604/110 |
| 4,677,756 | 7/1987 | Simon et al. | 128/776 X |
| 4,764,114 | 8/1988 | Jeffcoat et al. | 128/776 X |

OTHER PUBLICATIONS

Van Der Velden et al., "Introduction of A New Periodontal Probe: The Pressure Probe", J. of Clin. Periodontology; 1978:5; pp. 188-197.

Primary Examiner—Lee S. Cohen
Assistant Examiner—John P. Lacyk
Attorney, Agent, or Firm—Hopgood, Calimafde, Kalil, Blaustein & Judlowe

[57] ABSTRACT

A probe for measuring distances of clincal interest in a patient undergoing dental treatment has an end which is placed adjacent a first point and a tip which is extendable to a second point. A measurement apparatus in the housing, provides an output signal representative of the distance between the two points. An analyzer responsive to the output signal determines the distance. A friction mechanism assures that no more than a predetermined amount offorce is applied to the probe, making repetitive measurements accurate and avoiding damage to tissues. A microcomputer and printer analyze the data and present the data in a useful format. The tip of the probe is provided with storage apertures for use in delivering medication via the probe member. The probe is provided with an optical fibre cable and an optical encoder which is supported for rotary motion within the housing for eliminating cable twist evolved during manipulation. The tip of the probe is replaceable and provided with a frangible support which prevents re-use.

7 Claims, 20 Drawing Sheets

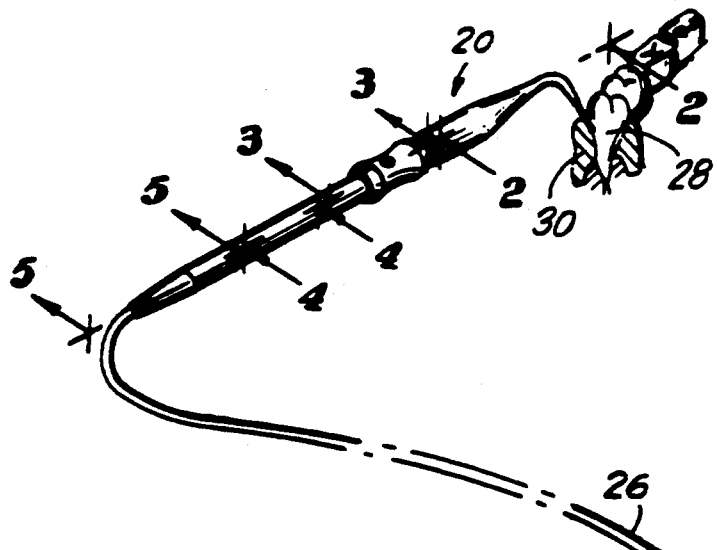
FIG. 1
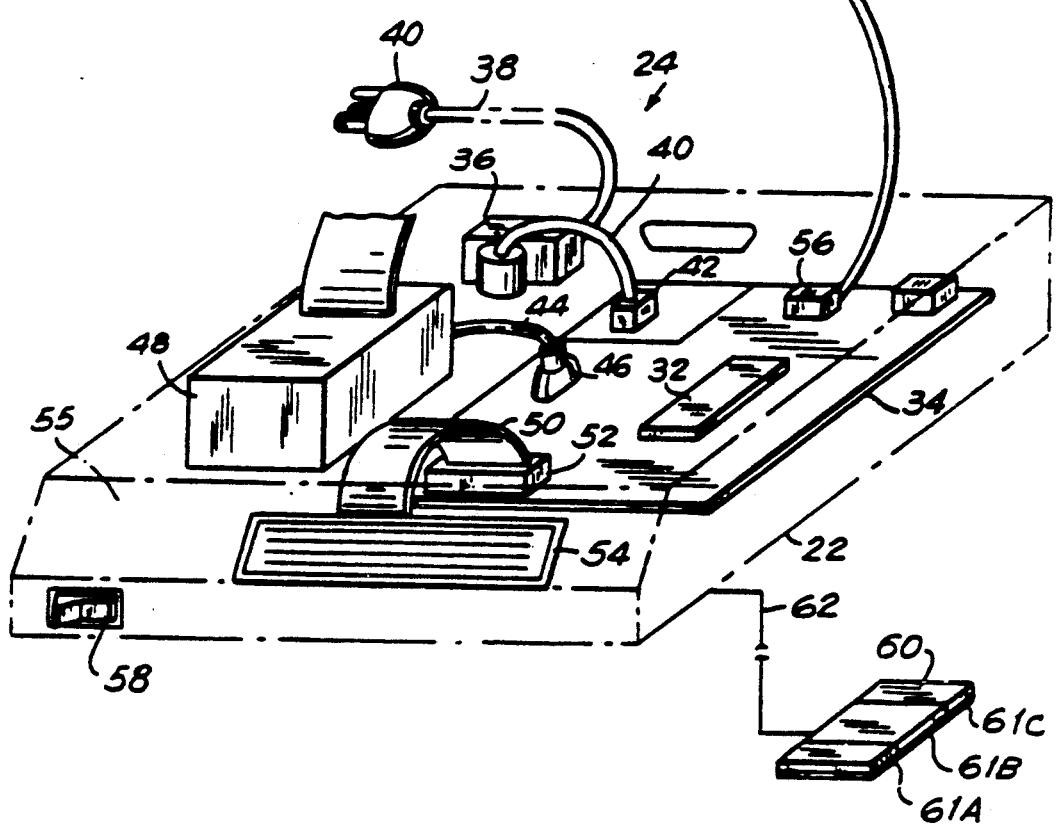

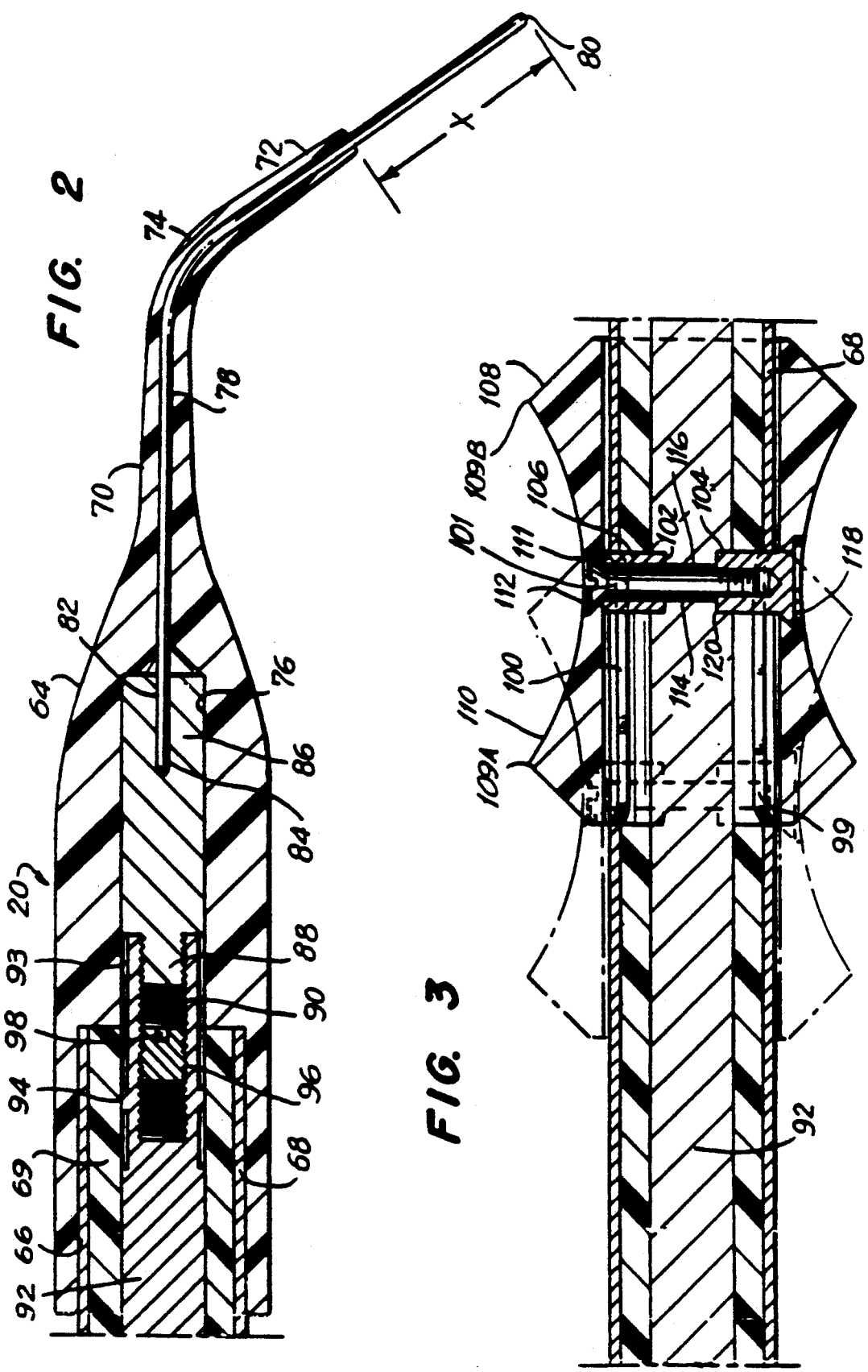

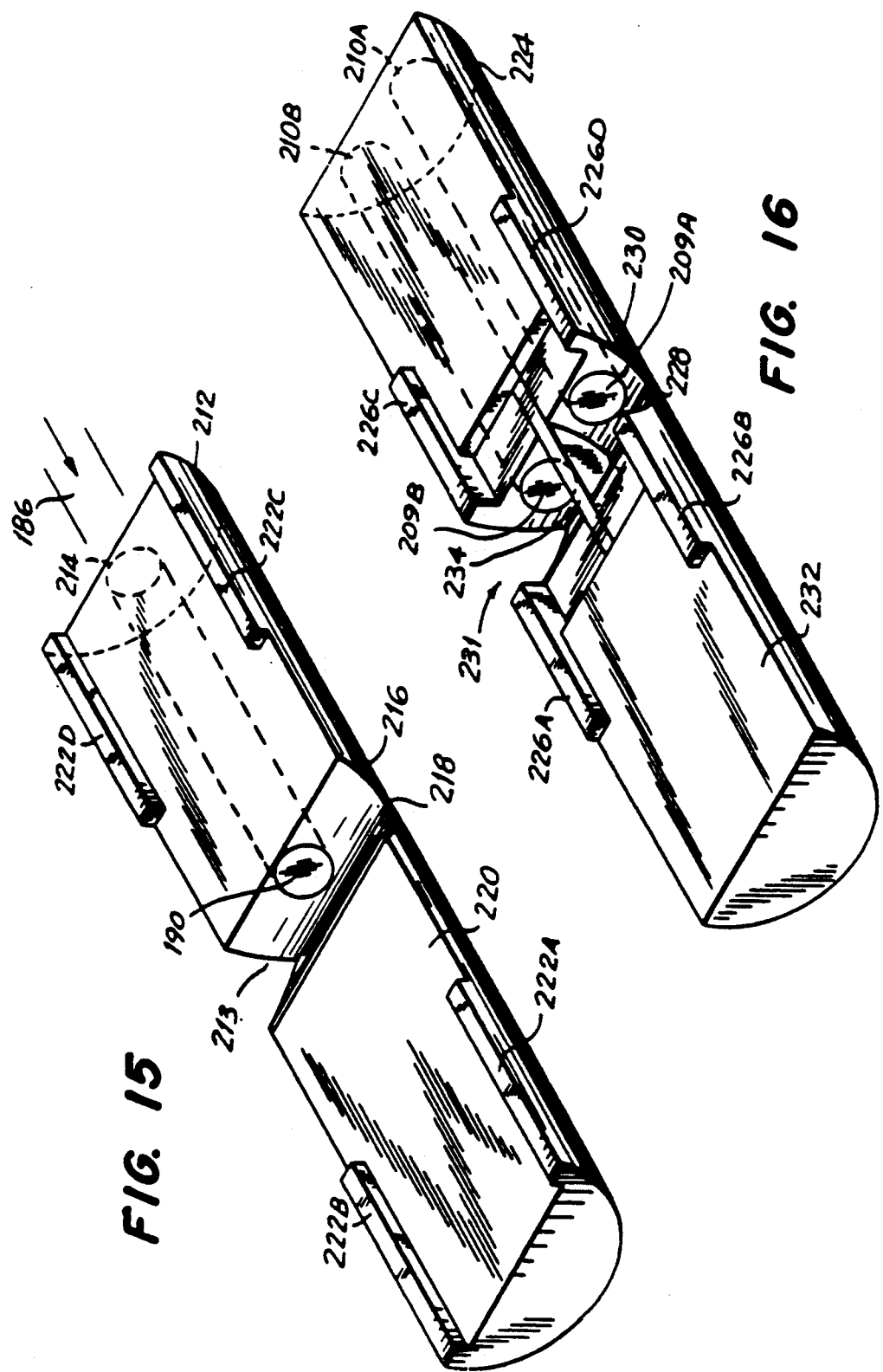

TABLE 1

ENCODER STRIP
MOVING TO RIGHT

CHANNEL

| A | B |
|---|---|
| 0 | 0 |
| 0 | 1 |
| 1 | 1 |
| 1 | 0 |
| 0 | 0 |
| 0 | 1 |
| 1 | 1 |
| 1 | 0 |
| 0 | 0 |

TABLE 2

ENCODER STRIP
MOVING TO LEFT

CHANNEL

| A | B |
|---|---|
| 0 | 0 |
| 1 | 0 |
| 1 | 1 |
| 0 | 1 |
| 0 | 0 |
| 1 | 0 |
| 1 | 1 |
| 0 | 1 |
| 0 | 0 |

FIG. 18A

TABLE 3

| | |
|---|---|
| 0 1 | OFFSET = 00 (=0) |
| 1 1 | OFFSET = 01 (=1) |
| 0 0 | OFFSET = 10 (=2) |
| 1 0 | OFFSET = 11 (=3) |

FIG. 18B

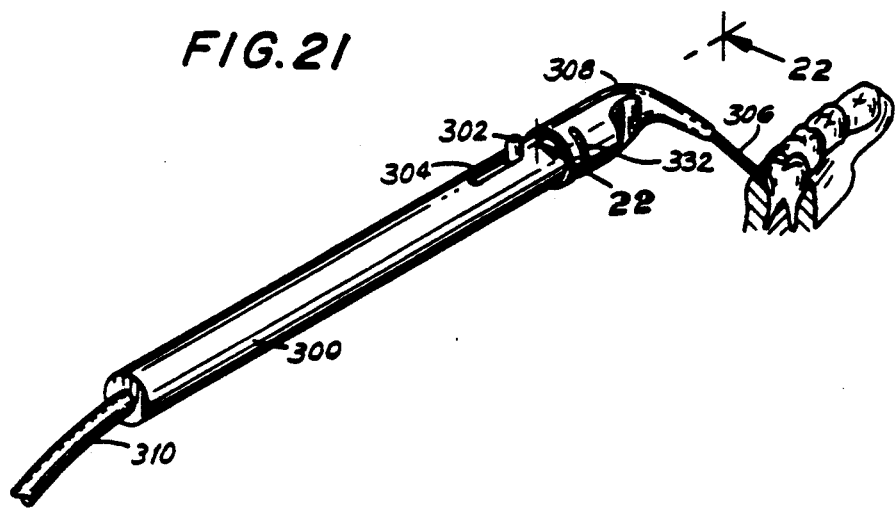
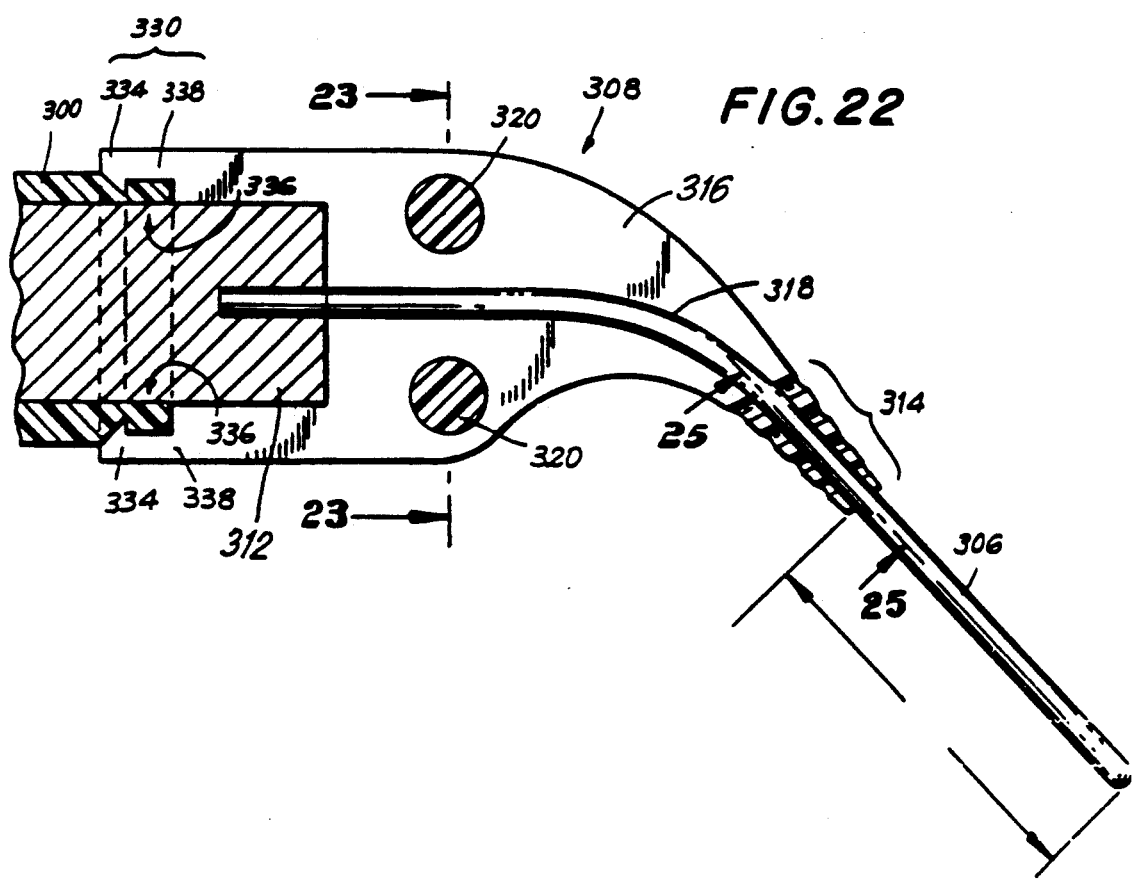

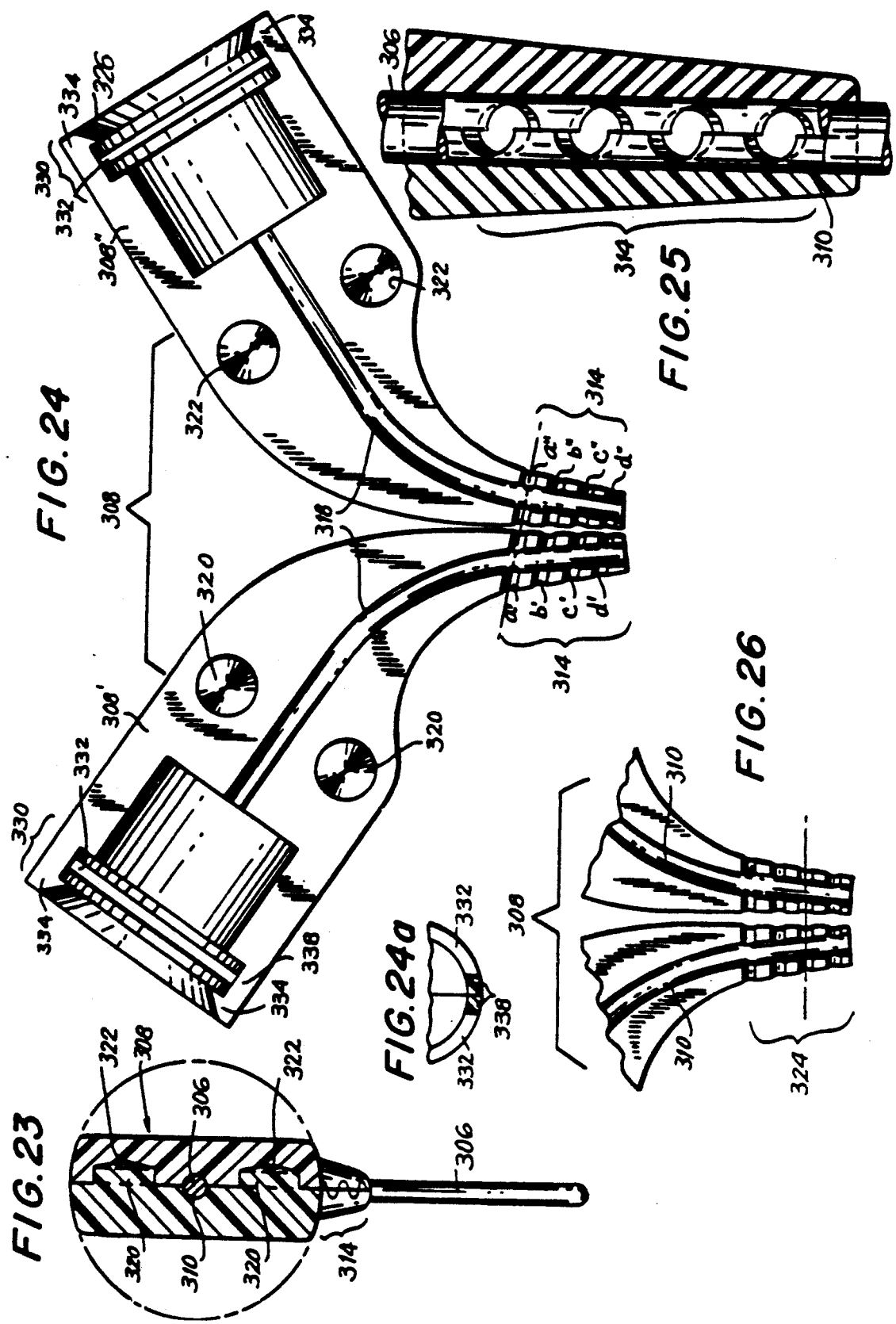

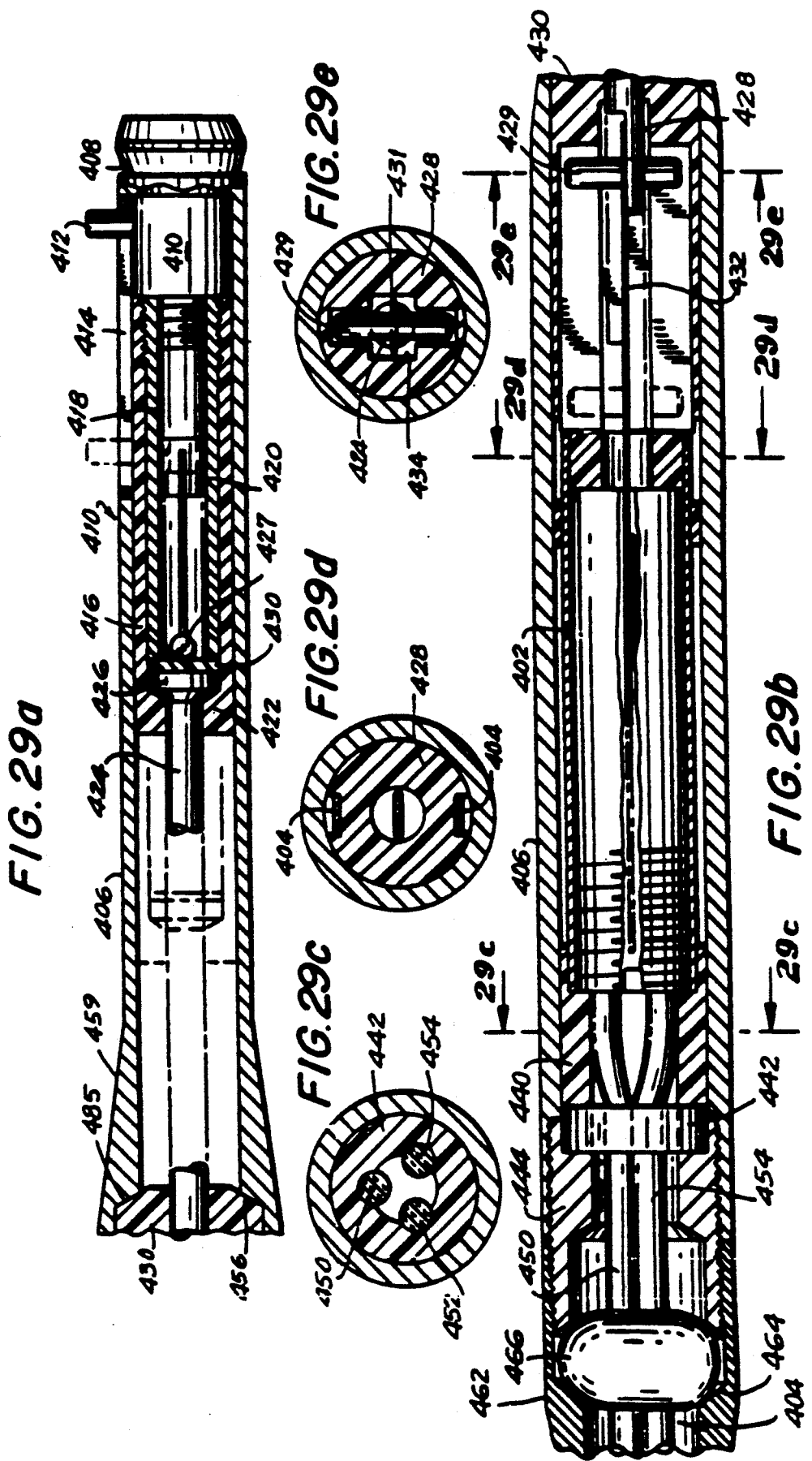

MEASURING PROBE

This application is a continuation, of application Ser. No. 024,991, filed Mar. 20, 1987 now abandoned which is a continuation-in-part of application Ser. No. 846,180, filed Mar. 31, 1986 now U.S. Pat. No. 4665621.

BACKGROUND OF THE INVENTION

The present invention is generally directed to a probe and measuring apparatus for use in dentistry and medicine and, in particular, for use in the accurate evaluation of periodontal pocket depth or during procedures that require the accurate evaluation of the depth of penetration and length of root canal.

One of the most useful diagnostic tools for determining the presence and severity of destruction due to periodontal disease is the pocket depth as indicated by the periodontal probe. By probing, small changes in attachment level and in pocket depth can be detected with a high degree of accuracy. However, the accuracy of the measurement is affected by the amount of force used, the diameter and shape of the probe, and differences between examiners. Further, in using conventional chart forms and techniques, recording of the data is time consuming and, when done without an assistant, requires interruption of the examination to record the data, followed by reinsertion of the probe. Further, evaluation of the progress of disease is best made on a chart which permits comparison of current and previous measurements.

Also, while conduction measuring devices can be used to determine when the apex of the root has been reached in root canal treatment, X-rays must be used when the root canal is being filled to determine whether packing is complete. It is, of course, undesirable to repeatedly X-ray a patient.

Finally, effective treatment of peridontal disease includes local application of antibiotic medication, such as tetracycline 1, while root canal procedures require filling of the root with sealant material.

Accordingly, there is a need for an instrument for probing gingival pockets, root canals, and the like, which provides precise, repeatable determinations of depth and which records, displays and charts data concerning depth of penetration in a manner useful to the practitioner without the use of x-rays. In addition, there is a need for a dental instrument which is capable of supplying medication, packing, and the like, to desired locations on or within a tooth.

SUMMARY OF THE INVENTION

The present invention provides an apparatus for measuring the distance between two points in a patient undergoing medical or dental diagnosis or treatment. The apparatus includes a housing having an end or tip which is placeable adjacent to one of the two points. When an elongate probe in the device is extended to the second point, a distance measurement device in the housing provides a measurement output signal which is representative of the distance between the two points. An analyzer responsive to the output signal reports the distance measured. The probe is connected to the distance measurement device and is slidably mounted in the housing, being extendable from one point to the other after the end of the housing has been put in place. The measurement device includes a motion detector which responds to motion of the probe in the housing to provide the output signal.

The probe is manually activated, and includes means to assure application of a relatively constant force to the probe to enhance measurement accuracy. The analyzer includes a microcomputer for analyzing the measurement data and displaying the results. Data which has been analyzed and displayed can also be printed on a printer or on a pre-prepared form by the printer. In one embodiment, the probe is electrically isolated from the analyzer by means of an optical signal cable and the probe is made rotatable, relative to the cable, to avoid the development of muscular fatigue in the hand of the practitioner.

The probe housing includes a tip for placement in the mouth of the patient, and is provided with openings which extend from the surface of the tip to a passageway in which the elongate probe travels. Medication stored in the openings can be delivered by extending the probe into contact with a point to be medicated. By adjustment of probe length, root canal filling material or sealant can be delivered to a tooth.

Accordingly, it is an object of the present invention to provide an apparatus for precisely and accurately measuring the distance between two points in a patient.

Another object of the invention is to provide an apparatus for conveniently recording and displaying the data obtained.

A further object of the invention is to provide an apparatus which permits accurate measurement of the depth of periodontal pockets with minimum discomfort and risk to the patient.

Still another object of the invention is to provide an apparatus wherein the variables associated with examination technique are eliminated.

Yet another object of the invention is to provide an apparatus which accurately measures the depth of a root canal.

A still further object of the invention is to provide an apparatus which permits delivery of medication or filling material to a tooth.

Still yet another object of the invention is to provide an apparatus for charting the results of a general dental examination.

Still other objects and advantages of the invention will in part be obvious and will in part be apparent from the specification.

The invention accordingly comprises the features of construction, combination of elements, and arrangement of parts which will be exemplified in the construction hereinafter set forth, and the scope of the invention will be indicated in the claims.

BRIEF DESCRIPTION OF THE DRAWINGS

For a fuller understanding of the invention, reference is had to the following description taken in connection with the accompanying drawings, in which:

FIG. 1 is a perspective view of an apparatus according to the invention;

FIGS. 2-5, respectively, are cross-sectional views taken along line 2—2, line 3—3, line 4—4, and line 5—5 of FIG. 1;

FIG. 15 is a perspective view of a housing portion for use with the encoder embodiment of FIG. 14;

FIG. 16 is a perspective view of a housing portion which mates with the housing portion illustrated in FIG. 15;

FIG. 18A is a chart showing data produced by the encoder of FIGS. 14 to 16;

FIG. 18B is a table used in computing direction and extent of motion in response to the data of FIG. 17;

FIG. 21 is a perspective view of a modified probe and tip according to the teachings of the invention;

FIG. 22 is a view in partial cross-section taken along lines 21—21 of FIG. 21;

FIG. 23 is a view in partial cross-section taken along lines 22—22 of FIG. 22;

FIG. 24 is an exploded view showing the two halves of FIGS. 21-23;

FIG. 25 is a view in partial cross-section taken along lines 25—25 of FIG. 22;

FIG. 26 is an exploded view of an alternate construction;

FIGS. 29a, 29b are a folded longitudinal partly sectional view of a second embodiment of a probe housing and encoder to the teachings of the invention;

FIGS. 29c-29e are partially sectional views of FIGS. 29a-29b.

DETAILED DESCRIPTION OF THE INVENTION

Figure 4:
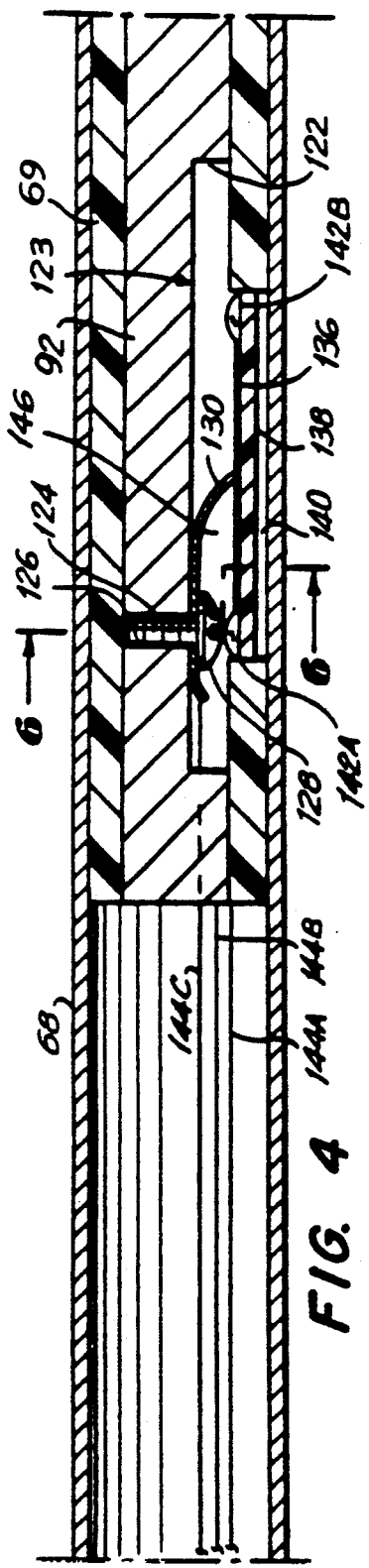

The present invention is directed to an apparatus for measuring distances between points in a patient undergoing medical or dental diagnosis or treatment. The invention also provides for the delivery of medication or filling material to the patient.

In the field of dentistry the present invention may be used to assist in the diagnosis of periodontal disease, to determine the depth of a root canal or the extent to which the gums have receded, to measure distances of interest in orthodontia, or to evaluate occlusive gaps between the teeth. The instrument can also be used for delivering medication or filling material to a tooth.

Reference is made to FIG. 1, wherein a dental probe 20 is used to measure distances between points in the mouth such as the length of the clinical crown of a tooth 28, the depth of a pocket between tooth 28 and the adjacent gum 30, or the depth of a root canal excavation (not shown). Data from probe 20, carried to a display unit 24 by a cable 26, is processed by a microcomputer 32 on a circuit board 34. Microprocessor 32 may advantageously be a single chip device such as one of the Mitsubishi 740 series having built in RAM, ROM, EPROM and A/D converter, the actual configuration being selected in accordance with the program requirements.

The power supply for circuit board 34 includes a transformer 36 which is connected by a power cord 38 to a plug 40 for a conventional power outlet. Power from the power supply is conducted to circuit board 34 by a cable 40. A connector 42, at the end of cable 40, mates with a corresponding connector (not shown) on circuit board 34.

Another cable 44 connects a compact printer 48 to circuit board 34 via a connector 46. A cable 50 connects a display 54 on front panel 55 to circuit board 34 via a connector 52. Probe cable 26 is connected to circuit board 34 by a connector 56. A foot pedal switch 60 is connected to circuit board 34 by a cable 62. Foot pedal switch 60 has three independent foot pedals 61A, 61B and 61C which supply signals to microcomputer 32 in unit 24 to select among possible modes of operation of microcomputer 32 for analyzing and organizing data from probe 20, as more fully described below. Cable 62 has a connector (not shown) for connecting cable 62 to circuit board 34. A switch 58 is connected to transformer 36 to control the supply of power to unit 24.

Referring to FIG. 2, a nylon tip 64 on probe 20 has a rear cylindrical opening 66 into which a probe housing 68 is fitted. Rear opening 66 and the outside of probe housing 68 are joined by an interference fit which provides just enough force to retain probe tip 64 but permitting removal of the tip by the application of reasonable force. A twist locking mechanism (not shown) may be used instead to removably secure probe tip 64 to probe housing 68.

Removable probe tip 64 has a conically tapered portion 70 which bends to a tip end 72 of smaller diameter. An elongate axial passageway 74 extends rearward from tip end 72 through tapered portion 70 to an opening 76 of larger diameter which connects to rear tip opening 66.

A probe member 78, which is preferably a nylon monofilament having a diameter of approximately 0.024 inch (0.61 mm) is closely received in passageway 74 so that it can slide therein. Probe member 78 may be radio-opaque so that it absorbs sufficient radiation to be visible in an X-ray of an area being probed.

The rear end 82 of probe member 78 is interference-fitted in an axial opening 84 of a chuck 86, being removable therefrom without damage by reasonable force. Chuck 86 has a threaded cylindrical portion 88 which is axially received in a cylindrical opening 90 of an actuating member 92. Cylindrical opening 90 is internally threaded and mates with an external thread on portion 88.

Outer wall 93 of actuating member 92 is of a smaller diameter than the internal diameter of a plastic internal housing sleeve 69. An annular shoulder 94 extends around the circumference of actuating member 92 between reduced sections thereof, and frictionally engages the inner surface of plastic housing sleeve 69. The force of the engagement is determined by the axial position of a screw 96 in central cylindrical opening 90; screw 96 may be rotated by means of a tool, such as an Allen wrench, inserted axially in screw opening 98. To this end, chuck member 86 is unscrewed from actuating member 92. Given that annular shoulder 94 is sized and shaped so as to contact the internal surface of internal sleeve 69, screw 96 is so sized so that, when turned towards the plane of annular shoulder 94, annular shoulder 94 is engaged against the inside of internal sleeve 69 with increasing force. Thus, the force needed to overcome friction between annular member 94 and the internal surface of internal sleeve 69 can be set by rotary adjustment of the position of screw 96.

To facilitate disconnection of chuck 86 from actuating member 92, the forward portion of chuck 86 is made non-circular in cross section so that rotation of probe tip 64 relative to housing member 68 rotates chuck 86 relative to actuating member 92. A corresponding non-circular cross section permits opening 76 to closely receive chuck 86 in probe tip 64, while permitting sliding of chuck 86 therein.

As depicted in FIG. 3, hollow cylindrical probe housing 68 and internal sleeve 69 each have diametrically opposed longitudinal slots 99 and 100. Two cylindrical flat-bottomed openings 102 and 104 are located on a common axis perpendicular to actuating member 92 and receive bushings 106 and 118, respectively. The inner diameter of a control sleeve 108 permits it to slide on housing 68. The outside surface of control sleeve 28 has spaced annular peaks 109A and 109B at either end of a concave peripheral surface 110. A screw 144 has a head 112 located in an opening 111 in surface 110 and extends through bushing 106 in opening 101, an interconnecting radial passageway 116 in actuating member 92, bushing 106, to thread into an opening 120 in bushing 118. The outer diameters of bushings 106 and 118 allow free longitudinal movement of the bushings in slots 98 and 100. Thus, sleeve 108 can be moved longitudinally onto probe housing 68 to move actuating member 92 and to cause probe member 78 to slide in probe tip 64. Slots 98 and 100 are so located that, when sleeve 108 is moved fully forward (to the right in FIG. 3), probe member 78 attains maximum extension (distance X in FIG. 2). Typically, full extension should be approximately 0.60 inches (1.5 cm) for most dental applications.

Figure 6:
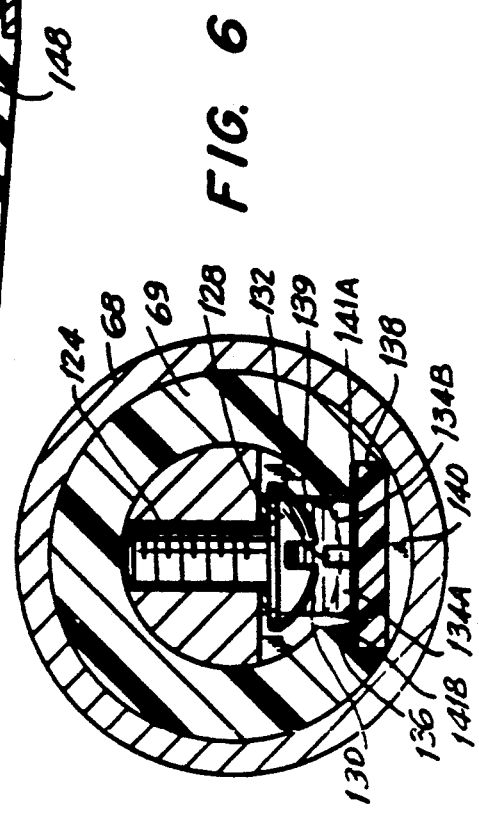
FIG. 6 is a cross-sectional view taken along line 6—6 of FIG. 4.

The rearward portion of probe 20 is shown in FIG. 4, where the rear end of actuating member 92 has a longitudinally extending radial slot 122 on whose bottom surface 123, the head of a radial screw 124 secures a resilient, conductive metallic member 130. Conductive member 130 has a longitudinal slot 132 (FIG. 6) to provide two portions 134A and 134B which contact a resistive element 136 formed on an insulating member 138. Insulating member 138 is fitted in probe housing 68 so as to be parallel to both the tangent of the inner surface and the axis thereof and to define a space 140 therebetween. In sleeve 69 an opening 139 receives metallic member 130 and shoulders 141A and 141B receive insulating member 138 (FIG. 6). Connection to each end of resistive layer 136 is made via electrical contacts 142A and 142B, respectively.

Figure 5:
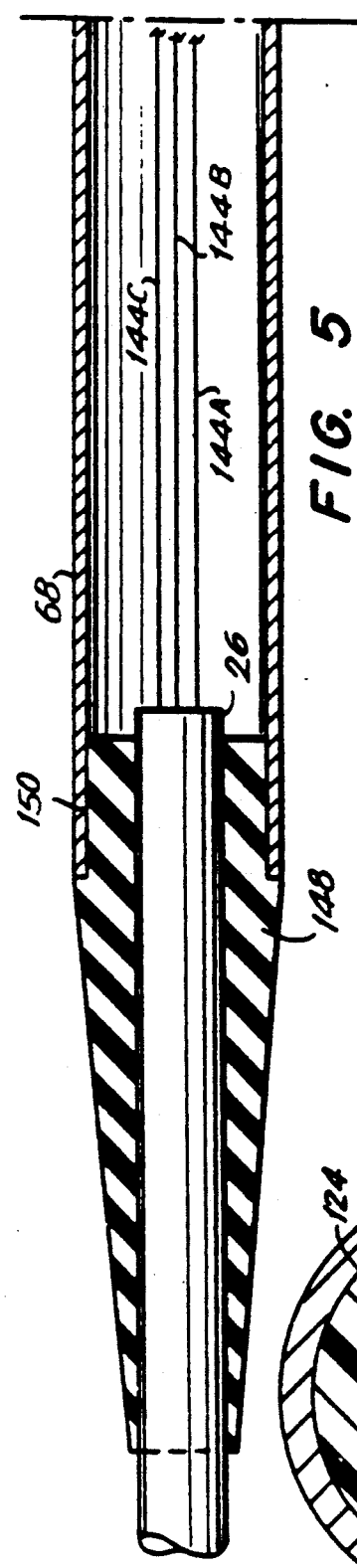

Contacts 142A and 142B connect (not shown) to wires 144A and 144B which extend from cable 26 (FIG. 5) through a passageway in internal sleeve 69. Cable 26 is held in a strain relief member 148 whose end portion 150 of reduced diameter fastens in the end of probe housing 68. A third wire 144C from cable 26 connects via contact screw 124 to conductive metallic member 130 and is long enough to accommodate full forward movement of actuating member 92 and probe member 78. When a voltage is applied to resistive element 136 via wires 144A and 144B, a potentiometer 146 is formed; therefore, movement of metallic member 130 along resistive element 136 results in variation of the voltage delivered to wire 144C. Thus, movement of actuating member 92 varies the voltage on wire 144C in proportion to the extension of probe member 78.

Figure 7:
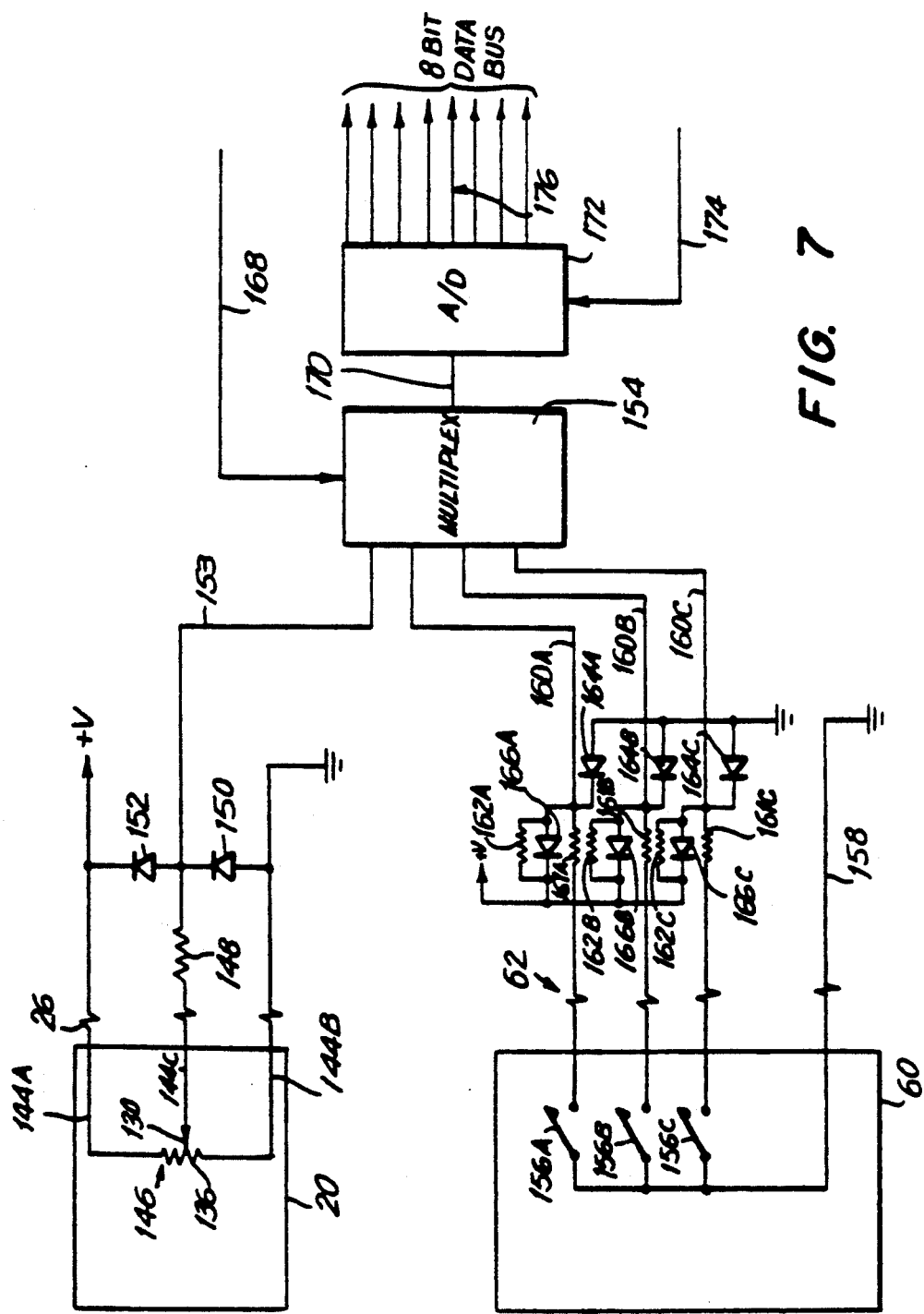
FIG. 7 is a schematic diagram showing the interconnection of various components illustrated in FIG. 1.

FIG. 7 shows the electrical circuit which connects probe 20 and pedal 60 to components on circuit board 34. One end of potentiometer 146 receives a low positive voltage V, e.g. 5 volts, from the power supply which powers microcomputer 34. The other end of potentiometer 146 is connected to ground. Wire 144C from metallic member 130, the slider of potentiometer 146, is connected to one end of a resistor 148. The other end of resistor 148 is connected to the junction of a first diode 150 and a second diode 152, the junction also being connected via wire 153 to one input of an analog multiplexer 154. Diodes 150 and 152 are normally-reverse biased, and protect against the build-up of damaging, excess potentials from static charges or induced voltages, at the input of multiplexer 154.

Foot pedals 61A, 61B and 61C each operate a respective enabling switch 156A, 156B and 156C. One side of each switch is grounded via a wire 158 in cable 62 with the other sides being respectively connected, via wires 160A, 160B and 160C in cable 62 and series resistors 161A, 161B and 161C, to three inputs of multiplexer 154. Each wire 160A, 160B and 160C is respectively connected via pull-up resistors 162A, 162B and 162C to supply voltage V and via diodes 164A, 164B and 164C to ground. Diodes 166A, 166B and 166C are respectively connected across pull-up resistors 162A, 162B and 162C. Thus, reversebiased diodes 164A, 164B, 164C, 166A, 166B, and 166C and the associated resistors form protection networks for the inputs of multiplexer 154.

A signal from microcomputer 32 to multiplexer 154 on control line 168 selects which of the four input channels to multiplexer 154 is connected through to the multiplexer output 170 at a given time. The mode selection function is controlled by the software program of microcomputer 32.

Multiplexer output is fed on line 170 to an analog-to-digital converter 172 which responds to a signal on control line 174 from microcomputer 32 at appropriate times to initiate conversion of the analog voltage signal on conductor 170 to digital form. The digital output is fed to microcomputer 32 on parallel data lines 176. The digital output of converter 172 represent a voltage of between zero and V volts generated by potentiometer 146 in probe 20, or it can be zero volts, or V volts, depending upon whether a selected switch 156A, 156B or 156C is open or closed.

When the system is turned on for measurement and identification of a gingival pocket, the program of microcomputer 32 initializes the system by clearing display 54 and displaying, for example, a tooth number designation "01 labial" and an initial depth reading of 00.0 mm. The program then causes the printer to print a header block identifying the instrument and forming a blank caption to be manually filled out by the dentist prior to start of the examination. The form has fields for "Date", "Time", "Patient" and "Examined By". The software then waits for a command from foot pedal switch 60.

In a typical operating sequence, sleeve 108 of probe 20 is placed at an appropriate position for zero reference calibration and a measurement is made. At least three methods are available for making measurements. In the first method, probe member 78 is withdrawn into probe tip 64 by moving sleeve 108 all of the way toward cable 26. Foot pedal 61A is now pressed, closing switch 156A, and establishing a zero reference from which measurements may be taken. The depth of a pocket associated with the first tooth is then measured by placing the end 72 of probe tip 64 on the labial side of the first tooth at the intersection of the gum with the clinical crown, that is, at the exposed lateral surface of the tooth. Sleeve 108 is then moved forward to extend probe member 78 from probe tip 64 until probe member end 80 reaches the bottom of the pocket. The dentist quickly develops a feel for when this has occurred. The voltage output of potentiometer 146 is now proportional to pocket depth and is represented as a positive number.

Using this method there is no reliance upon the friction adjusting mechanism discussed above, screw 96 being adjusted to provide only minimal friction to resist motion of sleeve 108. However, the second and third methods set forth below utilize the friction adjustment mechanism.

In accordance with the second method, foot pedal 61A is first pressed to provide a zero reference with probe member 78 fully retracted into probe tip 64. Probe member 78 is then extended fully, by moving sleeve 108, and inserted into the pocket being measured, probe 20 being manipulated, free of constraint on the motion of sleeve 108, until end 72 of probe tip 64 is at the intersection of the top of the gum and the clinical crown. The measurement of pocket depth is then taken by pressing foot pedal 61B.

In accordance with the third method, probe member 78 is first fully extended from probe tip 64 by moving control sleeve 108 all of the way toward probe tip 64. End 80 of probe member 78 is then inserted into a pocket to be measured, leaving end 72 of probe tip 64 positioned some distance from the intersection of the top of the gum and the clinical crown. Again with no constraint on sleeve 108, probe 20 is manipulated so that end 72 of tip 64 is moved to the intersection of the gum and the clinical crown. As with the second method, the amount of pressure exerted by end 80 of probe member 78 on the bottom of the pocket during the manipulation is determined by the position of screw 96. Via foot pedal 61A, closing switch 156A is closed to provide a zero reference. Sleeve 108 is then moved to fully retract probe member 78 into probe tip 64 and foot pedal 61B is then pressed to make a measurement which appears as a negative number.

In order to take a measurement in each case, foot pedal 61B is pressed to close switch 156B for the first measurement of a particular tooth. Printer 48 prints the tooth number, the designation lingual or labial, and then the depth reading. For subsequent measurements of the same tooth, only the depth reading is printed. Multiple measurements on the same tooth may be taken while switch 156B remains pressed, as a depth measurement will be periodically printed by printer 48 and shown on display 54. The position of end 80 of probe member 78 in the gingival pocket may be changed without withdrawing to decrease the chance of trauma.

To indicate a different location, such as the next tooth number, foot pedal 61C is pressed, closing switch 156C. At this time, the position of sleeve 108 in probe housing 68 determines whether the displayed tooth number is to be incremented or decremented. If sleeve 108 is moved to the rear when pedal 61C is pressed, the tooth number is incremented by one number and display 54 shows the next higher tooth number. If sleeve 108 is forward toward probe tip 64 when foot pedal 61C is pressed, the tooth number will be decremented by one and display 54 displays the next lower number with the appropriate lingual or labial designation.

Whether sleeve 108 is held at a position which causes incrementing or decrementing of tooth number, each time that foot pedal 61C is released and pressed again to close switch 156C, the incrementing or decrementing function is repeated. However, when pedal switch 61C is pressed continuously, repeated motion of sleeve 108 to either extreme of its motion, repeatedly causes respective incrementing or decrementing of tooth number.

In a typical examination sequence, it is advantageous to first increment tooth number from 16 labial as, for example, pocket depths on the labial sides of all lower teeth are examined. Then the program of microcomputer 32 switches to lingual and again indicates tooth number 16. Tooth number is again decremented from 16 to 1 as the lingual pockets of the bottom teeth are examined. After examination of the lingual side of tooth 1, the program causes upper tooth number 32 to be displayed, designating the labial side. Tooth number is then decremented as depths are measured until tooth number 17 labial is reached; tooth number 17 lingual is then designated and the process is continued until tooth number 32 lingual has been examined, completing the procedure. A hard copy printout of the measurements taken, with the location by tooth number and side (lingual/labial), is available to the dentist, the patient and other interested parties such as dental insurers.

Figure 8:
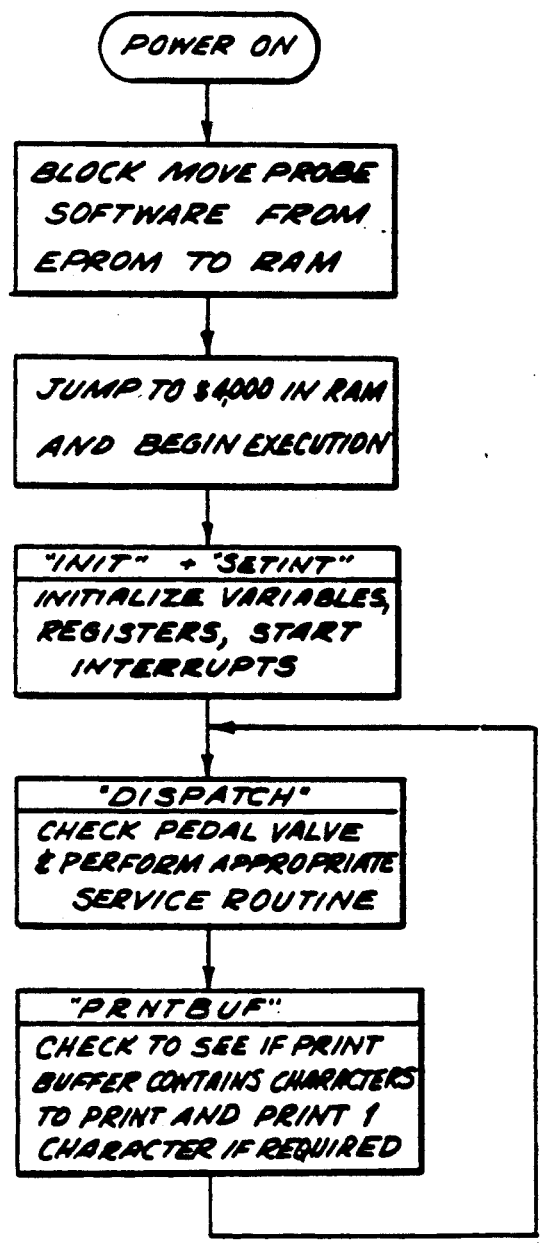
FIG. 8 is flow diagram of the main program executed by the microcomputer of the apparatus of FIG. 1.

The main flow diagram of the program which is executed by microcomputer 32 is shown in FIG. 8. Operation is initiated by turning on power switch 58. The program is moved from EPROM storage into a RAM area of microcomputer 32, and begins execution at location Hex.

First, the program executes subroutines INIT and SETINT to initialize all variables, the RAM area to be used by the program, and the CPU registers as well as to program an interrupt generator and to start the interrupts. After initialization, the program executes a subroutine, DISPATCH, which checks the current value of the foot pedal for task instruction by the operator, and performs the called service routine. Upon completion of DISPATCH, a subroutine, PRNTBUF, checks the CPU's printer buffer for contents to be printed. If something is found, the character (or characters) is sent to printer 48. The program then loops and returns to the top of DISPATCH, staying in this loop during normal operation of probe 20. While the loop executes on a continuous basis, it can be interrupted to perform other subroutines.

Figures 9, 10A:
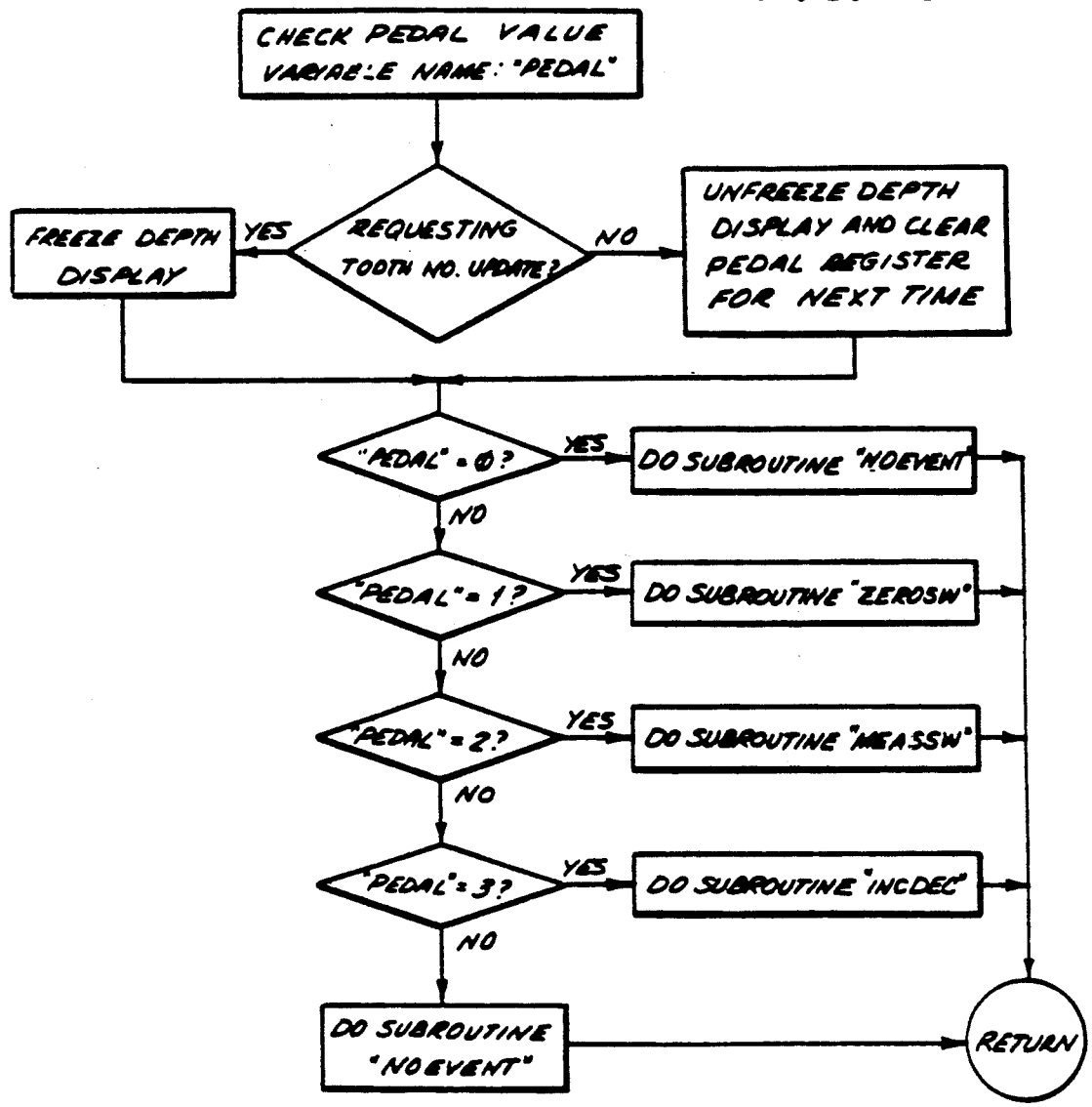
FIG. 9 is a flow diagram of a subroutine "DISPATCH" used to check the pedal value in the flow diagram of FIG. 8.
FIGS. 10A-10D are detailed flow diagrams of the subroutines, "NOEVENT", "ZEROSW", "MEASSW", and "INCDEC", respectively, of FIG. 9.

FIG. 9 details the subroutine DISPATCH. At the start of the subroutine, the value of the variable PEDAL is checked. E.g., which of pedal 61A, 61B or 61C, if any, is pressed is tested by supplying a sequence of signals to multiplexer 154 on line 168 (FIG. 7). The digital output appears on data bus 176 for evaluation and whether the tooth number is to be updated is tested.

If tooth update is requested, the current depth is frozen on display 54. If tooth update is not to occur, the display is not frozen and the pedal register is "cleared" for the next time through the foreground loop. The actual value of PEDAL is then determined and the appropriate subroutine is performed. If the PEDAL value is zero, no switch has been pressed, and subroutine NOEVENT is executed. If the PEDAL value is one, the program branches to the subroutine ZEROSW (zero switch). If the PEDAL value is two, the subroutine MEASSW (measure switch) is called. If the PEDAL value is three, the subroutine INCDEC is executed to increment or decrement the tooth number.

If for any reason a spurious code for the variable PEDAL appears in this subroutine, that is, if one of the four allowable values is not found, the program falls through to recovery mode because the spurious code is recognized as calling a no-event function (NOEVENT). At the end of whatever subroutine is called, control is returned to the foreground loop.

FIG. 10A details the subroutine NOEVENT which clears a repeat flag which indicates, if not set, that the INCDEC tooth number subroutine is being executed for the first time since the pedal press or, if set, that a subsequent iteration of the INCDEC subroutine is occurring.

Figure 10B:
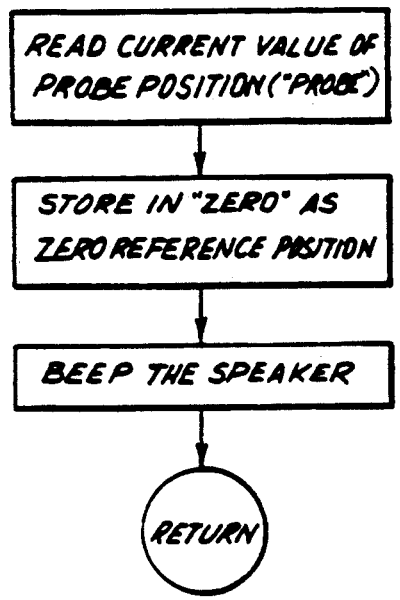

FIG. 10B illustrates the subroutine ZEROSW. In ZEROSW, the current position of probe member 78 relative to probe tip 64 is read first and the voltage value reported by A/D converter 172 in response to a signal on wire 144C, is stored as a zero reference value in variable ZERO. The latter will be subtracted from a current value, representing the relative position of probe member 78, obtained in taking a measurement. Thus, a signed number is obtained which indicates direction and displacement of the probe member since switch 156A was last closed. At this time, a beep signal from a loudspeaker (not shown) is supplied, telling the operator that the zero function has been executed, avoiding need for visual verification of display 54.

Figure 10C:
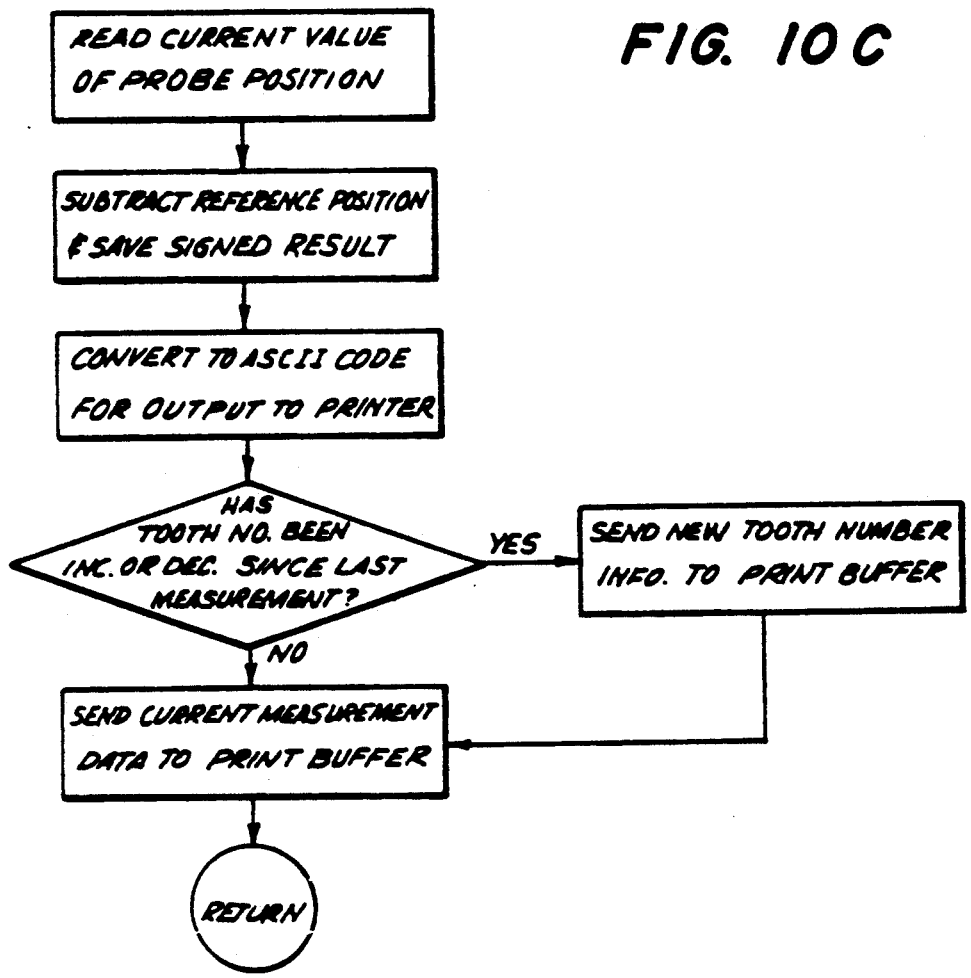

FIG. 10C illustrates the subroutine MEASSW (measure switch) which reads the current value of probe position and subtracts therefrom the value stored in variable ZERO reference. The signed result indicates direction and amount of displacement as of the time when the zero switch button was last pressed. This result is converted into millimeter units by a lookup table and then, by algorithm, into ASCII code for output to printer 48. The last part of subroutine MEASSW checks whether a measurement has been taken since the tooth number was last changed. If the measurement is the first since a tooth number update, the current tooth number is sent to the printer prior to recording the new measurement data. Control then returns to the calling subroutine, DISPATCH.

Figure 10D:
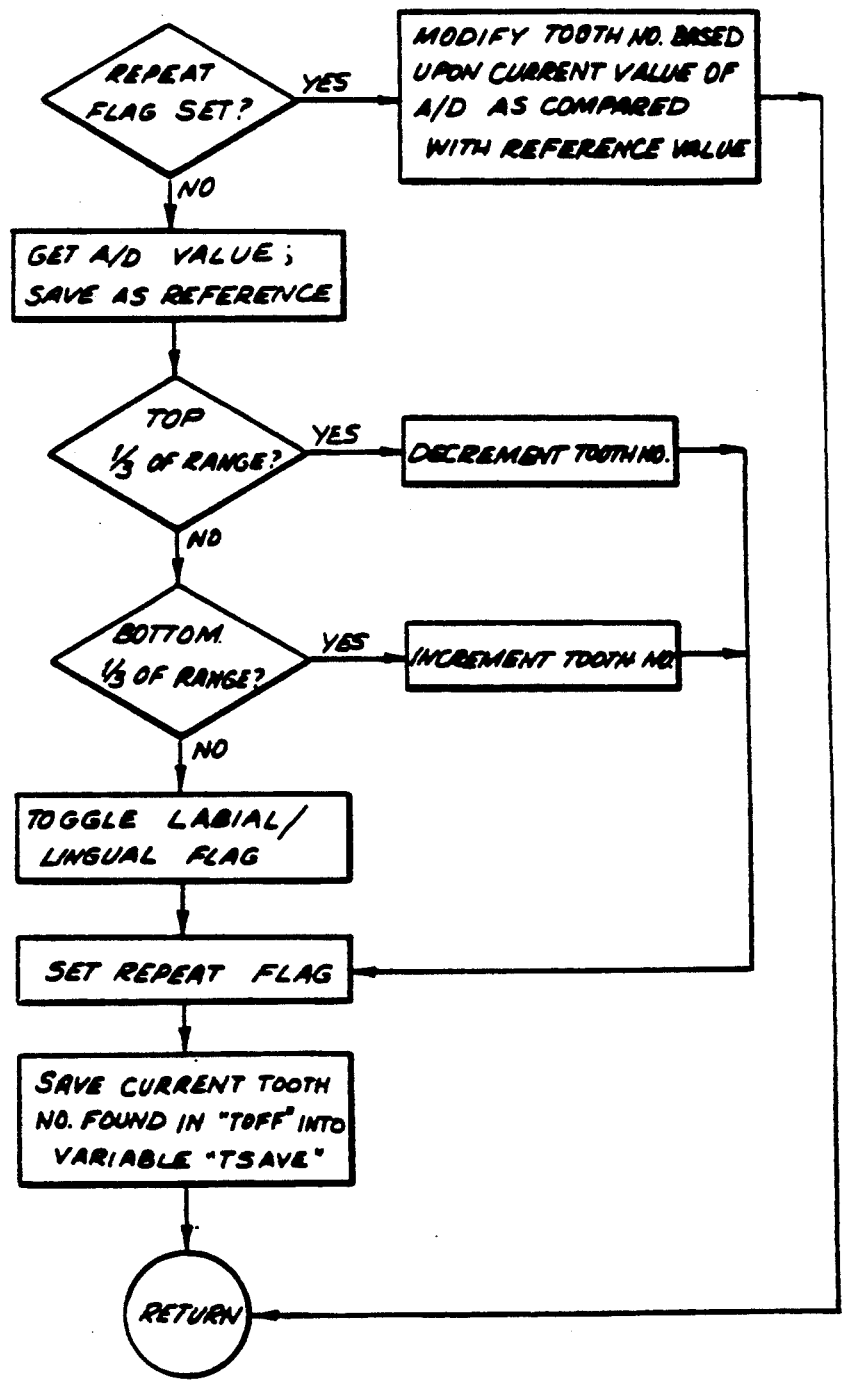

FIG. 10D shows the subroutine INCDEC, which is initiated when the tooth pedal 61C is pressed. INCDEC first checks the repeat flag (FIG. 10A) to establish whether the routine is being executed for the first time since the pedal was pressed, or whether it is a subsequent iteration in which the pedal has been held down since the last time INCDEC was executed. When the pedal is first pressed, the repeat flag not having been set, INCDEC signals multiplexer 154 on line 168 to convert the voltage from potentiometer 146. The output is saved as a reference value. The reference value is tested. If, due to the position of sleeve 108 on probe housing 68, it lies in the top third of the range of values, the tooth number is decremented by one. If it does not, the bottom third of the range is tested, and if it lies there, the tooth number is incremented by one. If both tests fail, the sleeve is located in the middle third of the range and a flag which controls whether "labial" or "lingual" is printed after the tooth number, is set. At this point, the repeat flag is set to show that the subroutine has been executed before.

During the foregoing, a current value for probe position has been saved as a reference and the operator has determined that the labial/lingual designation is correct. The value of the voltage produced by potentiometer 146 of probe 20 can now be read on a continuous basis to increment or decrement the tooth number as required.

After the repeat flag is set, the current tooth number, a variable TOFF, is saved in TSAVE, where it is available for display on the screen and as a zero reference from which positive and negative displacements are computed.

After the first execution of INCDEC, a return to DISPATCH occurs and DISPATCH returns to the main loop of the program. The next time the program is executed, INCDEC is again executed from the start. In this and subsequent executions, the repeat flag will be set and the path YES will be followed instead of the path NO. The tooth number will be modified as required based on the current position of sleeve 108 as compared to the reference value and the difference is applied to the reference tooth number in TSAVE. That is, the signed difference between the current value of probe position and the reference is used to cause a similar change in the tooth number based on the reference value in TSAVE.

Figure 11:
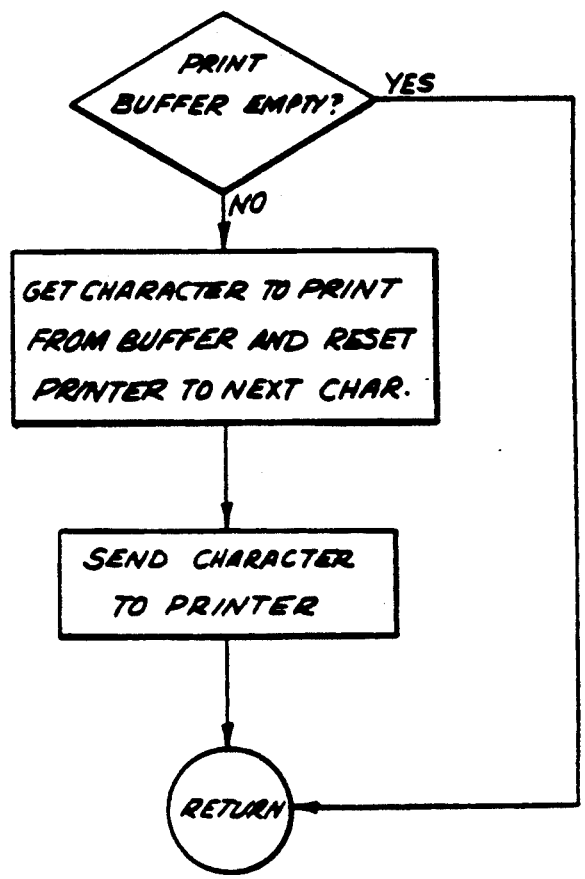
FIGS. 11-13 are, respectively, detailed flow diagrams of the subroutines "PRNTBUF" used in the main flow diagram of FIG. 8 and of first and second parts of an interrupt routine "DEBOUNCE" used to interrupt the program of FIG. 8.

FIG. 11 details the subroutine PRNTBUF (print buffer) which services a RAM-based buffer in which characters to be sent to the printer are stored. PRNTBUF determines whether there is anything to print; if the buffer is empty, the program returns to the main routine. If there is something in the buffer, the first character thereof is sent to the printer. The pointer is then updated, and return is made to the main program. One character is printed each time that the foreground loop executes. By printing in this manner, time is provided for microcomputer 32 to service other tasks such as updating the screen, reading the probe, and reading the foot switch. However, it appears that the microcomputer is doing all these things at once.

Figure 12:
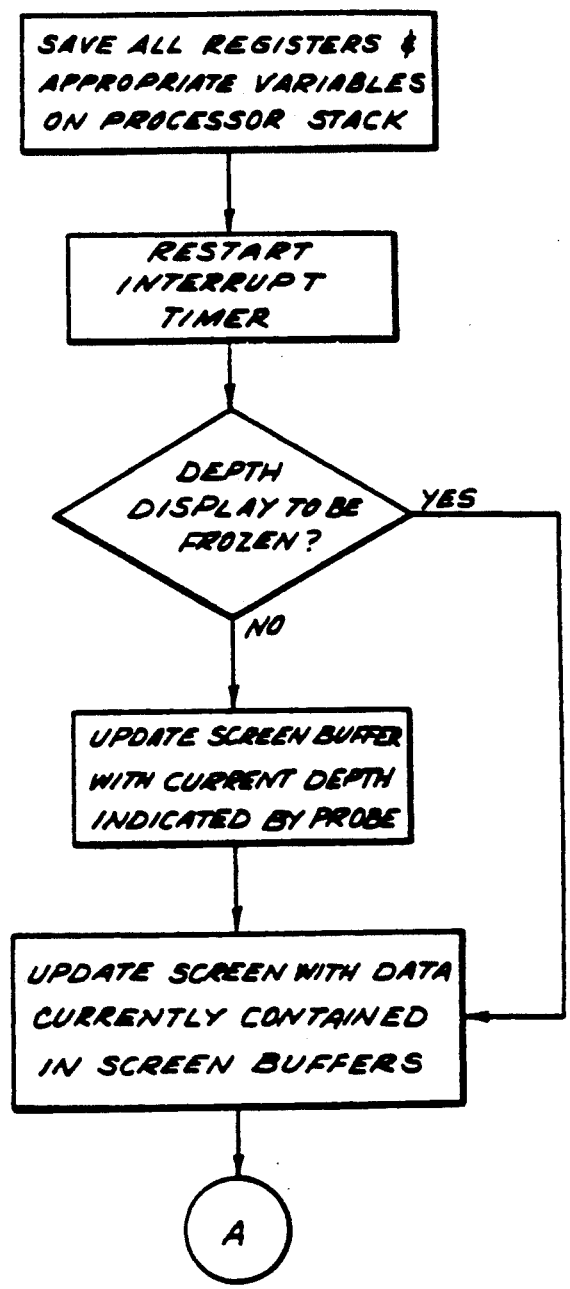

FIG. 12 details DEBOUNCE, a timed interrupt subroutine which reads the condition of the foot pedal switches and validates data so obtained. When an asynchronous event occurs, it is generally designated an interrupt; e.g. a hardware-initiated subroutine call is executed upon receiving a time-out from a counter.

When the transition from a program such as DISPATCH or MEASSW to DEBOUNCE occurs, the values in all the registers and any variables which may be required in executing DEBOUNCE, are saved on a processor stack in RAM memory. The interrupt timer is started again so that a constant time base continues. The period of the interrupt is approximately 40 milliseconds and DEBOUNCE is thus executed approximately 25 times every second. After the timer has been reset, a check is made to determine that the data displayed should remain the same, which is the condition which obtains when a tooth number change is being carried out. If tooth number is not being changed, a signal on line 168 causes the output of potentiometer 146 to be read and the current output value of the analog-to-digital converter is stored in a screen buffer for later display. If the tooth number is being changed, the program bypasses this set of instructions to prevent simultaneous change of tooth number and depth measurement on the display. At this point the program accesses the various buffers associated with the displayed material and the information is updated.

When point A is reached in the subroutine of FIG. 12, a subroutine (FIG. 13) is executed which periodically samples the condition of the foot pedal switch 60. First, whether pedal switch 156A, 156B or 156C is closed. If no switch is closed, all the variables associated with the DEBOUNCE algorithm are reset and all the original variables and registers are restored to their state prior to occurrence of the interrupt. The foreground loop of the program then takes up from the point where the interrupt routine began. If one of switches 156A, 156B or 156C is found to be closed, the program then determines whether or not the value provided is that which was found the last time this interrupt was executed. If the value is the same, the dentist desires to continue to execute the present foot pedal function.

Since approximately 25 checks are run each second, the particular event the dentist is interested in can happen much too quickly. To slow down the response time, twelve or thirteen interrupts are counted before the function is finally called; the desired function is thus repeated approximately every half second. After the half second delay, the code in the variable PEDAL (which is then used by the DISPATCH routine to direct the equipment to do whatever is required) is rewritten. The program then exits the interrupt routine, restores the variables, and returns to the main program loop.

Figure 13:
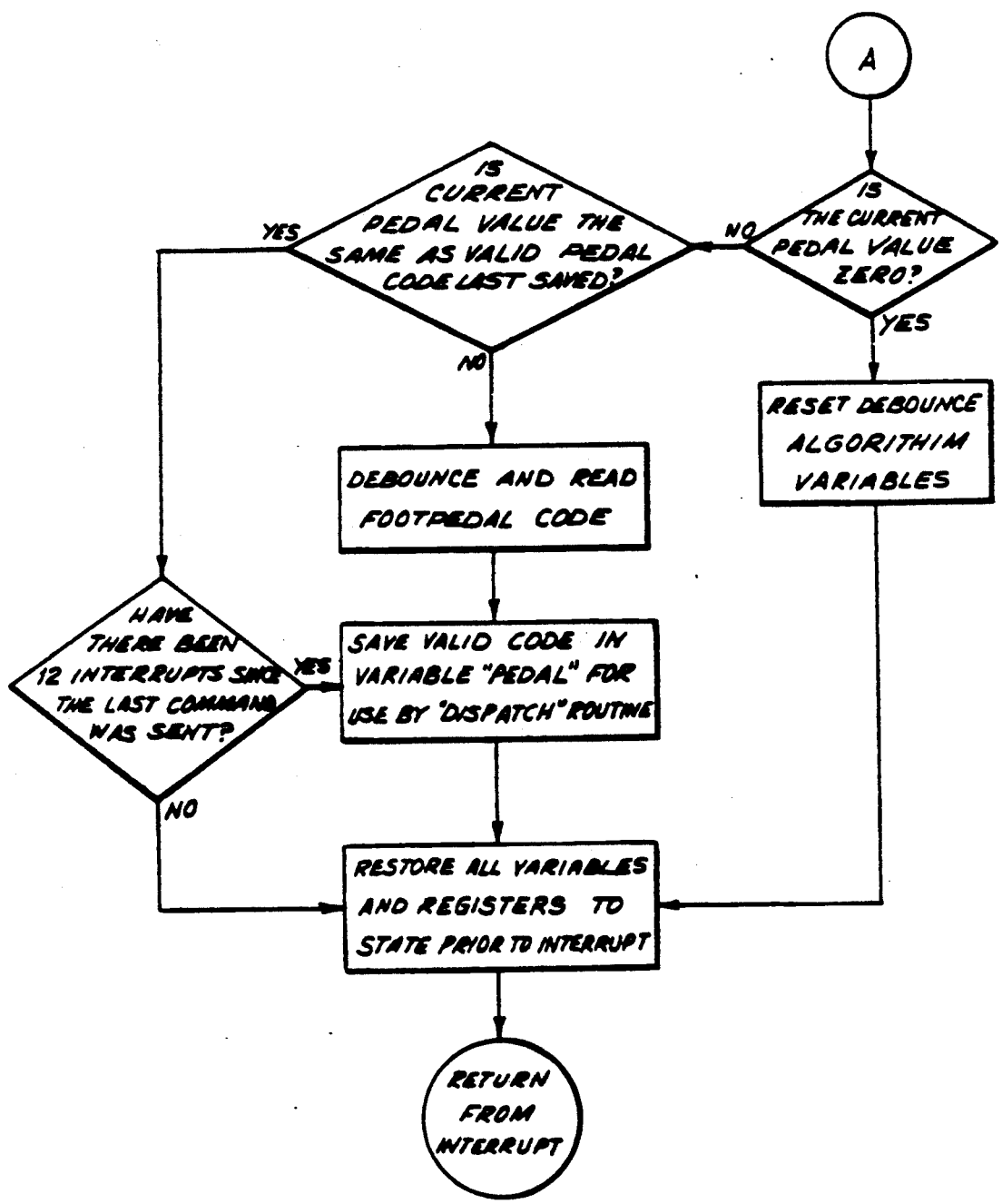

A third condition is possible when starting from letter A of FIG. 13. First, a non-zero pedal value is found and that value is then found to be different from the value of the previous interrupt. Such is the case if, for example, PEDAL was zero (no switch had been pressed) and then had been pressed for the first time. If the pedal value is different, a series of program steps is executed which debounce the foot pedal switches, to assure that a valid value has been obtained, by reading the code from the pedal several times, thereby verifying that the value of PEDAL is stable and is not spurious. If the value of PEDAL is determined to be an actual command, the appropriate value is stored in the variable PEDAL for use by the subroutine DISPATCH. After DEBOUNCE has executed, program control returns to the main loop.

Figure 14:
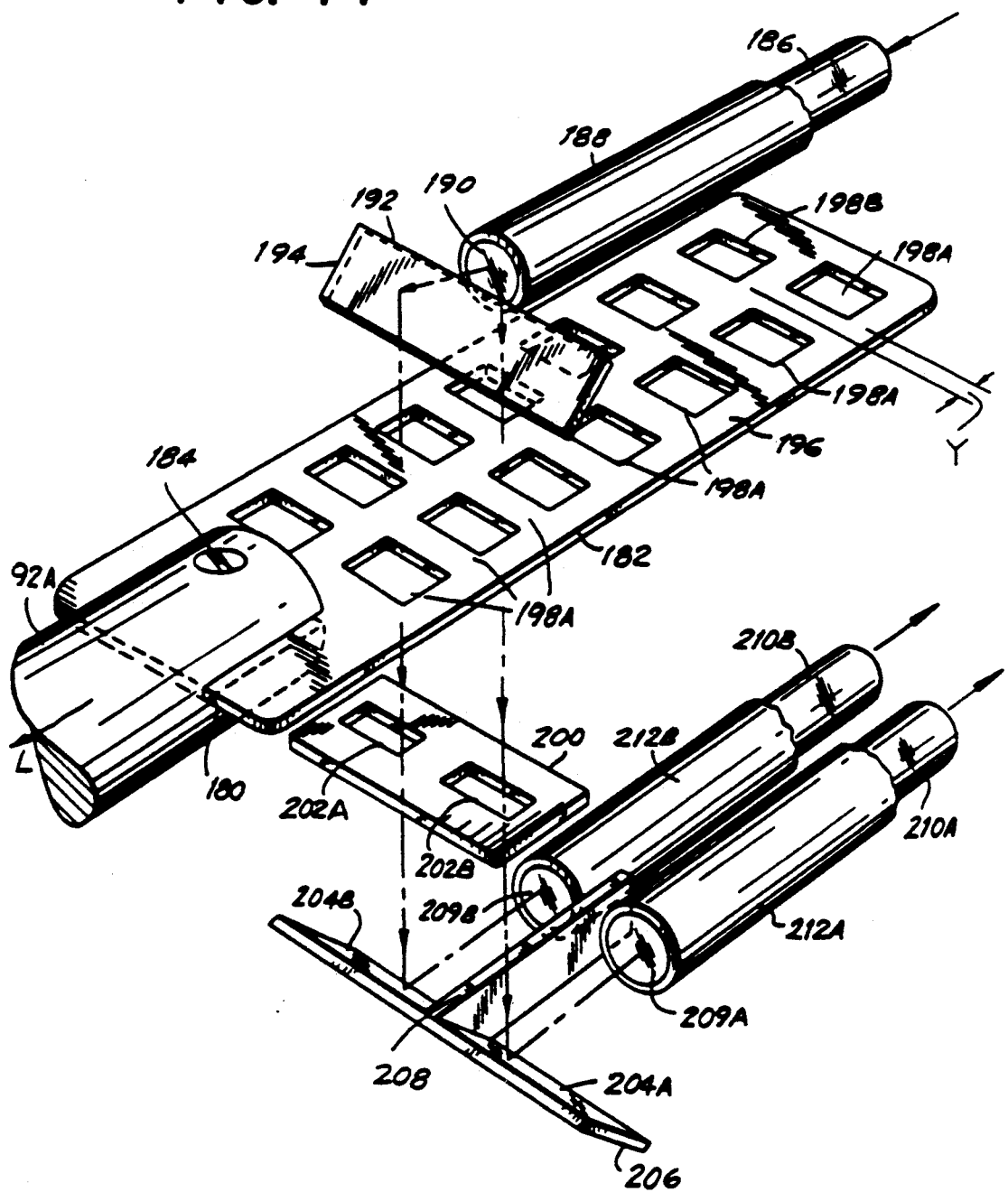
FIG. 14 is an exploded, perspective view of an embodiment of an encoder for the apparatus illustrated in FIG. 1.

FIG. 14 is an exploded perspective view of an embodiment of the probe of the invention in which direct electrical connections to the probe are eliminated, thereby obviating the need to take precautions, even with the low voltages of the probe of the first embodiment, to protect the patient from electrical shock. In FIG. 14, an actuating member 92A, similar in structure and function to actuating member 92 of FIGS. 1–6 has a diametrically-extending end slot 180 instead of the longitudinal slot 122 of FIG. 4. An opaque card 182 is secured in slot 180 by a screw 184 which extends into the slot through a radially extending hole from the outer surface of actuating member 92A. A light conductor 186 of, for example, plastic fiber whose entire length is enclosed by an opaque covering 188, conducts light from a light source to and through an end surface 190. Light from the end surface is reflected by a mirrored surface 192 of an upper reflector member 194 and then travels perpendicular to the major surface 196 of an encoder card 182. Encoder card 182 is provided with a first longitudinal series of openings 198A and a second, parallel series of openings 198B. Openings 198A and 198B are all of equal size, being respectively spaced apart along the length of card 182 by identical equal distances. However, the longitudinal positions of openings 198A are staggered, relative to the positions of corresponding openings 198B, by a distance Y between like margins. For example, if the openings 198A and 198B each have a dimension along the card 182 of 0.50 mm, and the spacing between openings 198A and 198B is also 0.50 mm, the distance Y is preferably 0.25 mm, providing a resolution of 0.25 mm in measuring motion of card 182. The relative position of the edges of openings 198A relative to those of openings 198B provides a unique sequence of output light pulses for each direction of motion of card 182 under control of actuating member 92A.

To this end, light which has passed through openings 198A and 198B in card 182 then passes through openings 202A and 202B, respectively, in a light baffle 200. The light from openings 202A and 202B impinges upon reflective surfaces 204A and 204B of a lower reflector 206 which is supported by an opaque separator 208. Separator 208 acts as a light baffle between the lower relecting surfaces and between input surfaces 209A and 209B of fiber light conductors 210A and 210B. Opaque coverings 212A and 212B are provided along the entire lengths of light conductors 210A and 210B so that the light which impinges upon end surfaces 209A and 209B is conducted therein. Covered light conductors 186, 210A and 210B are formed into a fiber optic cable (not shown) similar to cable 26 for conveying data from probe 20 to circuit board 34 in housing 22. Housing 22 contains both a light source (not shown) for supplying light to fibre optic light conductor 186 and suitable photodetection means for converting pulses of light received from conductors 210A and 210B into electrical signals. These components can be of a type well known in the art such as the transmitter/receiver pair sold by Molex ® Corporation as Part No. 15-75-0002 and described in Application Note 15M entitled "Fiber Optic Links" published in October of 1985. Pulse-conditioning circuits, also described in Application Note 15M, for converting the electrical signals into pulses useful as inputs for microcomputer 32, are also located on circuit board 34.

FIGS. 15 and 16 illustrate a probe housing for encoder of FIG. 14. An upper housing member 212, shown inverted in FIG. 15, is generally elongate and has a substantially semicircular cross section. Light conductor 186 is received in an axial opening 214 in member 212 so that its end surface projects into a V-notch 213 of member 212. V-notch 213 has sides 216 and 218 which are each at a substantially 45° angle relative to planar upper surface 220 of member 212. Surface 218 has a reflective coating which reflects light from conductor 186 in a direction perpendicular to the longitudinal axis of member 212. Surface 218 serves the same purpose as the mirrored surface 192 of FIG. 14.

Upper housing member 212 has two sets of circumferential projections 222A, 222B, and 222C, 222D which extend from either end of member 212 towards V-notch 213. Lower housing member 224 (FIG. 16) has complimentary pairs of projections 226A, 226B, and 226C, 226D on either side of V-notch 231. When assembled, upper housing member 212 fits onto lower housing member 224 with the outward ends of projections 226A and 226C respectively abutting the inward ends of projections 222A, 222C, and with projections 226B, 226D of lower housing member 224 similarly abutting the projections 222B, 222D of upper housing member 212. When assembled, upper housing member 212 and lower housing member 224 form a substantially solid cylindrical body having a wide, longitudinal slot, bounded on either side by projections 222A–222D and 226A–226D in which card 182 is slidably received.

In operation, light from fiber optic conductor 186 is reflected by reflector surface 218 and directed through openings 198A and 198B of encoder card 182 (FIG. 14). Light passing through the card is reflected from forward surface 228. Surfaces 216 and 218 define V-notch 213 in upper housing part 212 and surfaces 228 and 240 define lower notch 231. Surfaces 228 and 230 are disposed at an angle of substantially 45° relative to planar longitudinal surface 232 of lower housing member 224. An opaque axial separator 234 in lower housing member 224 functions as separator 208 of FIG. 14 so that light reflected from surface 228 travels to end surfaces 209A and 209B of fibre optic conductors 210A and 210B respectively.

When assembled, upper housing member 212 and lower housing member 224 fit within inner sleeve 69 of probe 20 and, together with card 182, provides an optical encoder of the extent and direction of motion of actuating member 92 and of probe member 78.

While optical encoder card 182 and light baffle 200 are shown in FIG. 14 as made of opaque material having openings 198A, 198B and 202B, through which light can pass, it will be understood by those skilled in the art that other structures may be used. For example, photographic negative material may be exposed and developed so as to provide an opaque area through which light will not pass, sound surrounding clear areas, appropriately located, through which light may pass.

Figure 17:
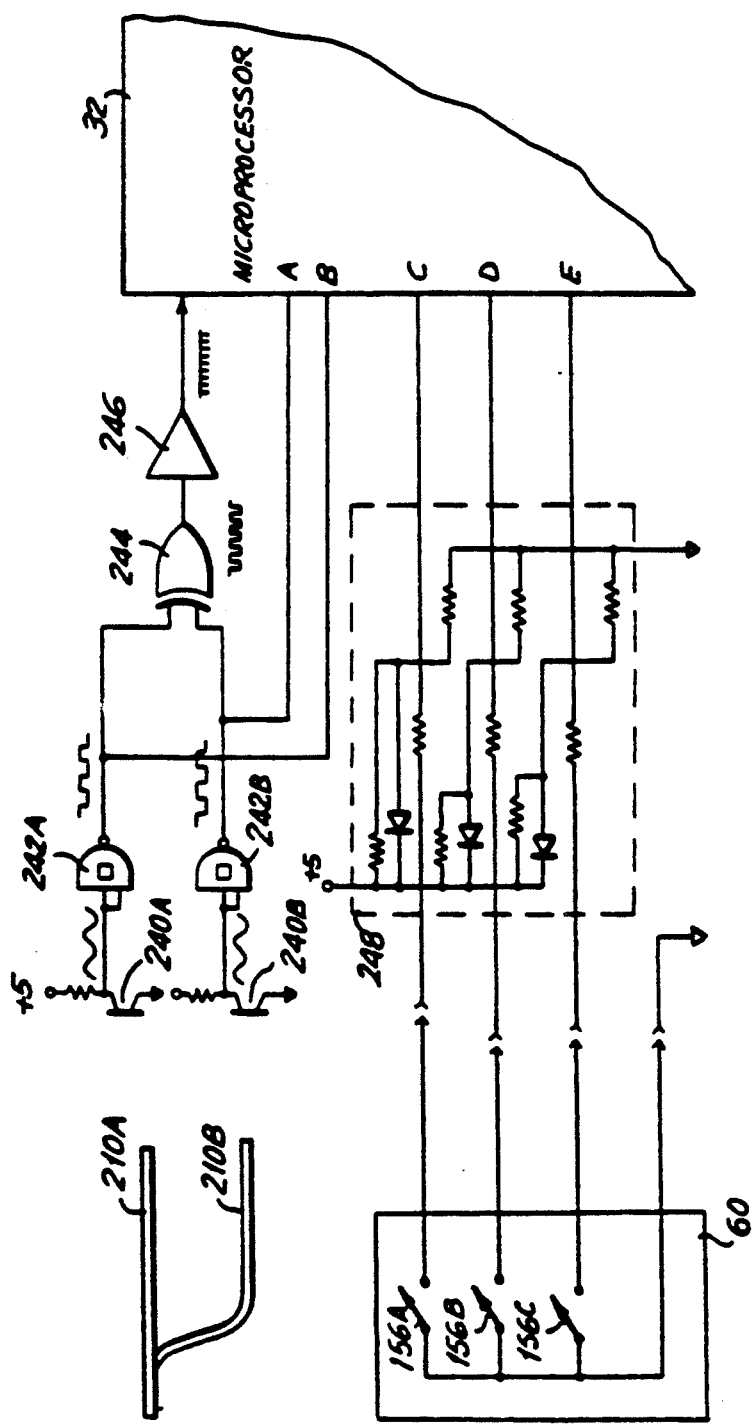
FIG. 17 is a schematic diagram showing the interconnection of components when the encoder of FIGS. 15 and 16 is used.

FIG. 17 illustrates a modified interface used with the optical encoder of probe 20. Photodetectors 240A and 240B, which may be receivers of the type mentioned above located on circuit board 34, respond to light signals from fiber optic conductors 210A and 210B. Schmitt-trigger logic gates 242A and 242B, respectively, condition the outputs of photodetectors 240A and 240B into square waves. The resulting pulse trains are fed into an EXCLUSIVE-OR gate 244. The output of gate 244 is fed to an edge detector 246 which produces a pulsed output each time that a transition is detected.

When encoder card 182 is moved, the light from fibre optic conductor 186 is interrupted and light pulses are transmitted to photodetectors 240A and 240B. Due to the spacing and positioning of the two sets of apertures on card 182, detection of a transition on either channel signals displacement of 0.25 mm and the specific positive or negative states immediately before and after the transition indicate the direction of travel. Thus, each time a transition occurs in either channel, edge detector 246 inputs a pulse to gate 244. The pulse output of edge detector 246 is fed to a non-maskable interrupt input of microprocessor 32, causing it to increase or decrease the current position of the probe member by 0.25 mm.

Figure 19:
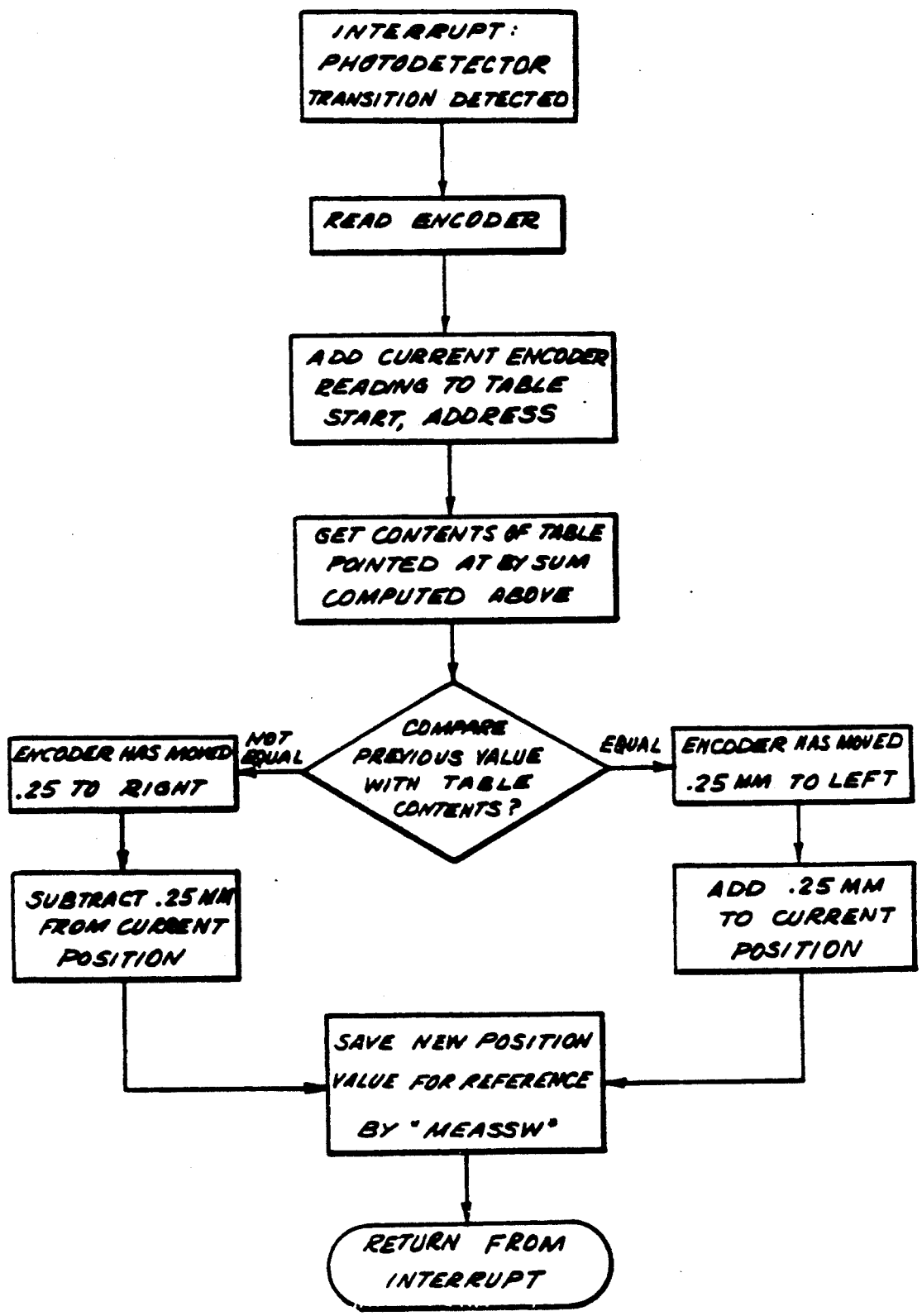
FIG. 19 is a detailed flow diagram illustrating computation of direction and extent of motion the data of FIG. 18.

The interrupt subroutine of FIG. 19 enables microcomputer 32 to determine whether the probe displacement was positive or negative by reading the status of Schmitt-trigger gates 242A and 242B via two bits A and B (FIG. 18A) fed to an input port. The current and previous states of the bits are compared and 0.25 mm is either added or subtracted to the current measurement value. To this end, the data from foot pedal switch 60 passes through a static protection circuit 248 like the one of FIG. 7, to be fed to three input ports C, D, and E of microcomputer 32. Since foot pedal switches 156A, 156B and 156C provide digital signals, no A/D conditioning is required.

When using the encoder of FIGS. 14 to 16, switch 61C must be closed before sleeve 108 is moved in order to modify tooth number, since there is no absolute reference for the position of card 182.

FIG. 18A shows, in chart form, the data produced by Schmitt-trigger logic gates 242A and 242B with channel A showing light pulses associated with conductor 210A and channel B showing pulses associated with conductor 210B. Tables 1 and 2 also show how the data is produced when card 182 moves to the right and to the left, respectively, showing the sequence of pulses produced as a direct result of the staggered placement of openings 198A and 198B, the sequence of pulses produced when card 182 moves to the left being the reverse of that produced when card 182 moves to the right.

FIG. 18B is a lookup table for use with the interrupt routine of FIG. 19 and FIG. 19 depicts the steps for computing the direction and extent of motion of probe member 78 to produce a value for insertion in the first block of subroutine MEASSW of FIG. 10C when the optical encoder is used. The subroutine of FIG. 19 is executed each time that edge detector circuit 246 detects a transition in a photodetector input. First, the digital data at input ports A and B is read, formatted as a binary number between zero and three, and added to the beginning address of a four byte lookup table containing data pertaining to travel in the left direction. If the data pointed to by this sum is equal to the data read at the last transition, the travel was leftward; if the data is not equal, the travel was rightward. The program then increases or decreases the current probe position by 0.25 mm, as appropriate. The current probe position number is the value provided by the A/D converter of FIG. 7.

The invention can be modified in various ways. For example, a series of switches may be provided on housing 22 and/or on a pendant attached thereto to facilitate the use of location routines other than those previously illustrated, such as a complete clinical examination. The switches provide inputs to microcomputer 32 at times selected by the software configuration for changing the predetermined location sequence, allowing use of diagnostic routines which follow different standards. Further, means may be provided for the entry or storage of previous data so that data of both current and previous measurements of, for example, gingival pocket depth, can be printed out, enabling the progress or recession of periodontal disease to be followed.

Figure 20:
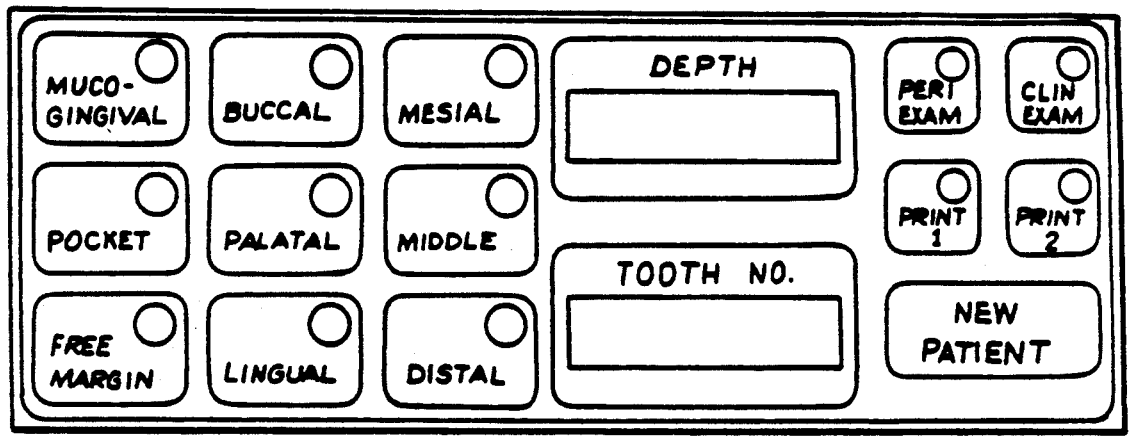
FIG. 20 is a plan view of an alternate control panel for use with the apparatus of the invention.

An example of a set of membrane switch labels intended for use with a program for reporting data for a variety of measurements and observations, made during a periodontal examination is illustrated in FIG. 20. In FIG. 20, pressure on any one of the rectangular or square areas (outlined in heavy ink) will cause the recording of data at an appropriate location on a chart. For example, on a dental chart having a series of sixteen columns corresponding to the upper or lower sixteen teeth, the lefthand side of the chart could include a series of downward labels such as "muco-gingival line", "pocket depth", and "margin free of gingiva". A similar column on the righthand side of the chart would be labeled "mesial", blank, "distal" at three points in each of the horizontal columns corresponding to the three labels in the lefthand column. Thus, spaces would be provided for data at three locations in each of the categories specified. These locations would be specified at the time observations were taken by pressing the appropriate membrane area to activate the switch thereunder.

The apparatus of the present invention can assist in determining the depth of packing of a root canal by moving probe member 78 by control sleeve 108 to assist in placing material in the root canal as further set forth below. When used in this manner, the apparatus provides an indication of the depth to which the material has penetrated along the root canal. In this context, the location specified for a measurement by operation of the apparatus can be that of a root, instead of a tooth number.

The apparatus of the present invention may also be used to measure the gap between teeth at occlusion. A special tip may be provided to allow bite spacing measurements. Since such distances are generally smaller then those measured when evaluating gingival pockets or root canal depth, sufficient resolution must be provided.

The printer need not necessarily be an integral part of the housing. A standard 8½ inch printer, such as the Epson MX-80, may be used in conjunction with the data collection apparatus of the present invention, making possible the use of standard or special periodontal forms to enhance presention or to provide a report in familiar form. Indeed, with appropriate software and controls, the apparatus may be used for recording data in routine or special dental examinations. The software then acquires, stores and prints clinical observations as to tooth condition, as well as various numeric values of pocket depth and the like in the appropriate locations on an appropriate form, graphically annotating the tooth illustrations as is commonly done by hand. Different forms or even, in certain cases, blank paper combined with appropriate output formatting routines, enable the device to perform a broad array of functions, including comparisons and printout of past and current data. To this end, data may be communicated to a separate computer via an output port, or the microprocessor of the apparatus itself can be elaborated to perform these tasks. To this end, the patient's dental, periodontal, etc. history may be stored on a floppy disk, updated, and utilized with readily available statistical and graphical software, and can effect, for example, a meaningful presentation of the progress or recession of a patient's periodontal disease, using dedicated pushbuttons on the housing to control menu-driven software, printing, downloading, uploading, measurement units, scaling, special report annotations, statistical analysis, graphical reporting, etc.

It is desirable for the apparatus of the present invention to be flexible to permit adaptation to new procedures as they are identified or developed. The use of uploading includes the capability to accept instructions which would modify some aspect of normal operation or provide new functionality, including, for example, changing report format data. Further, a powered actuator for moving the probe member can replace or supplement the manual control sleeve of the probe. For example, mechanical power can be delivered from the circuit board 34 to actuating member 92 via a flexible, but substantially inextensible elongate member, such as a rigid plastic or steel wire.

FIGS. 21 through 26 illustrate a second embodiment of the distance measuring probe of the invention. In this embodiment, the outer housing 300 (FIG. 21) of the probe is made of stainless steel and finger pressure is applied to a rounded finger knob 302 which projects outwardly of housing 300 through longitudinal slot 304 for moving probe member 306 in and out of detachable plastic tip 308. An optical encoder, like that of FIG. 14, is enclosed within housing 300 and is connected by a cable 310 to a control and display apparatus of the type described above.

Tip 308, in addition to providing a passageway 318 (FIG. 22) within which flexible probe member 306 is moved by chuck 312, in the manner previously described, includes a plurality of capillary openings 314a–314d which are located in tip region 316 adjacent to the end of tip 308 (FIGS. 22-25). The openings are used for storage of medication for delivery to selected locations in the mouth of the patient via probe member 306. For this purpose, tip region 316 can be dipped into a container of medication and the openings allowed to fill themselves. Since, as depicted in FIG. 22, the openings 314a–314d intersect and cross the passageway 318 in which probe member 306 travels, medication placed therein is brought into contact with the surface of probe member 306. When probe member 306 is retracted into tip 308, the contained length of probe member 306 becomes coated with the medication. When the tip member is subsequently pushed out of the tip, the medication will be delivered to whatever point in the mouth of the patient is brought into contact with the probe member by the practitioner.

Probe tip 308 is fabricated in two halves (FIG. 24). Subsequently, the two halves are mated and then joined by applying pressure to buttons 320 to cause them to expand and be held in recesses 322 (FIG. 23), in a manner well known in the art. One half of 308' (FIG. 24) of tip 308 has a set of semicircular storage openings 314a'–314d' and the other half 308" has openings 314a"–314d". Each set of openings traverses the axis of passageway 310 at an angle of about 80 degrees and, when the two halves are joined (FIGS. 23 and 25), the openings of one set cross the openings of the other set at passageway 310. The result gives an appearance of misalignment of the ends of the openings on the lower surface of tip region 316 (FIG. 23), whereas the end openings are correctly aligned on the opposite surface, as can be seen by inspection of FIG. 24. Other arrangements of the medicament openings in the region of the tip are, of course, possible. Thus, as shown in FIG. 26, openings 324a–324d can be made orthogonal to passageway 310. Another set of openings (not shown) can be provided at 90° to the depicted openings, doubling the amount of storage volume.

FIGS. 21, 22 and 24 also illustrate a safety feature of the invention which provides for one-time use of detachable tip 308, insuring against transfer of germs, infection, and the like, from one patient to another. According to this feature of the invention, each rear portion 330 of probe 308 is provided with a breakaway portion flange 334 of triangular cross-section which seats and interlocks in a mating peripheral groove 336 on the forward end of plastic housing 300 (FIG. 22). To this end, the rearward facing, perpendicular, forward wall of groove 336 mates with the oppositely-facing perpendicular walls of flange sections 334 to retain tip 308 on housing 300, after it has been put in place. Breakaway flange portions 334 are two semicircular halves which are each respectively connected to one of the halves of probe 308 by a pair of breakaway supports 338, as shown in the partial cross-section of FIG. 24, leaving semicircular empty spaces 332 between themselves and the respective probe halves.

The two tip halves 308' and 308" of FIG. 24 are joined at the factory and the complete tip 208 is supplied to the user. The fresh, sterile tip is applied to the forward end of housing 300 by slight pressure. The diameter of housing 300 is of a slightly smaller diameter forward of groove 336, so the sloping surfaces 326 of flange portions 334 can readily pass thereover to seat in recess 302 (FIG. 22). To this end, breakaway supports 338 bend slightly, without breaking. When, however, the tip is to be removed after use, the forward, plane surfaces of retainer flanges come into direct opposition to the radial surfaces of groove 336, and the force of removal causes supports 338 to break. As a result, breakaway flange portions 334 are permanently disconnected from the main body of probe tip 308, rendering the probe tip incapable of further use.

Figure 27:
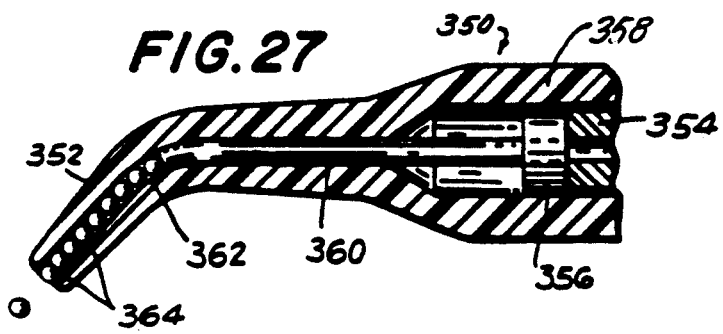
FIG. 27 is a view in partial cross-section of a tip modified to deliver another form of medication.
Figure 28:
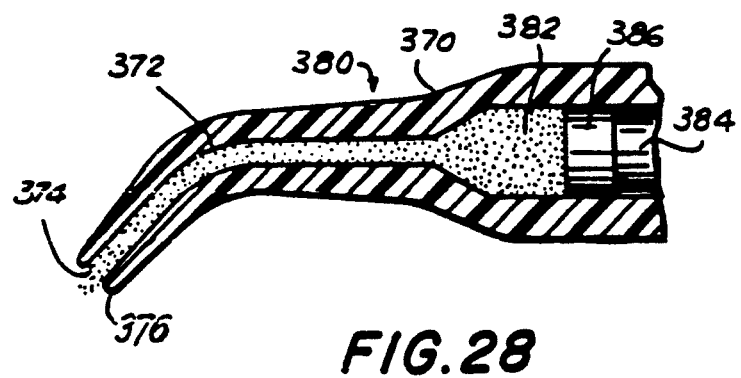
FIG. 28 is a view in partial cross-section showing still another embodiment of the invention for delivering material to a patient.

FIGS. 27 and 28 are sectional views of embodiments of the invention which are useful for delivering medication, filling material, and the like, to selected locations in the teeth, gums, or other tissues of a patient. In the embodiment of FIG. 27 a probe tip 350, having an angulated end portion 352, is adapted to receive the housing (not shown) and the end of a chuck 354 like that of chuck 86 (FIG. 2). Probe tip 350 has a cylindrical piston disk 356 which is slidably fitted in a rearward, axially-oriented cylinder 358 and which is contacted by chuck 354. A foreshortened, flexible probe member 360 is fastened on piston 356 and extends forward thereof in probe tip passageway 362. Probe member 360, being flexible, can easily follow the angulation in the passageway when it is moved forward. When retracted, probe 360 leaves the outer portion of passageway 362 free to receive one or more wicks 364 which are saturated with medication. When pushed by chuck 354, the number of wicks delivered can be metered by the distance-measuring apparatus of the invention. As depicted in FIG. 27, the wicks are each about a millimeter long so that a change of one millimeter in the digital depth displayed, for example, in FIG. 20, would indicate that one wick had been delivered from the tip. Thus, the effect of force transmitted from the practitioner's finger via clutch 354, piston 356, to probe member 360 can be monitored to determine the amount of medicated packing which has been delivered.

Another probe tip structure useful for treatments is shown in FIG. 28, where probe tip 380 contains, forward of clutch member 384, a cylindrical, free piston disk 386. The cylindrical axial space 382 within which piston disk 386 is slidably received communicates at its forward end, via conical section 370, with passageway 372. When tip 380 is mounted on the end of a housing (not shown) of the invention, the force of the practitioner's finger transmitted by clutch member 384 to piston disk 366, causes material 374 which has been prepacked in space 382 and passageway 372 to be extruded out of probe tip end 376 in a manner similar to a syringe. As with the tip of FIG. 27, the associated measurement apparatus is programmed so as to indicate the quantity of medication or other material dispensed.

The embodiments of FIGS. 27 and 28 are advantageous in that they provide a convenient way of supplying medication or filling material in known quantity. Also, the time required to deliver the material is minimized, since the probe tips can be prepacked, either in the practitioner's laboratory or in the factory. They also permit the rapid replacement of tips to deliver large filling quantities, instead of the customary, alternate manipulation of syringe and measurement probe.

FIG. 29 is an illustrative embodiment of a probe structure which is particularly useful with the optical encoding and optical cable arrangement set forth above in connection with FIGS. 14-16. It has been found, in using the probe of the invention with a fiber optic cable, that the cable, while flexible to a degree, is nevertheless relatively rigid. Thus, in rolling the probe to achieve a desired angle of probe member relative to his work, the practitioner must exert considerable force. This can result, after a period time, in muscle strain and cramps.

The foregoing problem is solved in the probe of FIG. 29 by placing the encoder in a mounted encoder tube 402 so that the attached fiber optic cable 404 will be free to rotate within probe housing 406.

The forward portion 408 of probe housing 406 and the enclosed chuck structure 410 are like those shown in FIGS. 2 and 22 in that the forward portion is peripherally grooved at 408 to receive and mate with a removable probe tip and in that a flexible probe member (not shown) is received in chuck 410. Chuck 410 is movable by finger pressure applied to knob 412 between the forward position shown in solid lines and the rear position shown in dashed lines. Knob 412 projects radially from the body of the chuck for moving the chuck axially within probe housing 406. A longitudinal slot 414 in the wall of housing 406 guides finger knob 412 in its fore-and-aft motion, while preventing rotation thereof.

Also contained within the forward end is a friction adjustment assembly which performs the same pressure-sensitive slip-clutch function as that described in connection with FIG. 2. In this case, the clutch includes a friction clutch sleeve 418 which is threaded into an anti-friction sleeve 416. Sleeve 418 is expandable by operation of set screw 420 in the manner described above, and is threaded onto the rear portion of chuck. Anti-friction sleeve 416 is closed at its rearward end by a wall 422 which contains an axial opening through which an axial encoder shaft 424 passes. The forward end of encoder shaft 424 carries a head 426 which is joined thereto by means of a conical under-surface 428; the latter seats on a mating forward-facing conical surface of wall 422. An anti-friction disk 430 of glass-filled teflon material is placed between the rearward end of friction sleeve 418 and the top surface of encoder shaft head 426, so that when friction sleeve 418 is screwed into anti-friction sleeve 416 and fixed therein by transverse pin 427, encoder shaft head 426 is embraced against fore-and-aft motion, substantially without play, while a substantially friction-free surface permits encoder shaft 424 and encoder shaft head 426 to rotate freely. Encoder shaft 424 extends to the rear, ending in a longitudinal flat portion 428 to which an opaque encoder card 432 is attached by pin 429.

Encoder tube 402 threadedly receives two encoder housing members like those of FIGS. 15 and 16 above. Encoder card 432 is axially movable within the encoder housing in response to axial movement of encoder shaft 424 coupled thereto by pin 429 as the probe member is moved in and out, and is protected against rotary motion by longitudinal side walls 434 (FIG. 29e) formed in the body of a central anti-friction sleeve 416. Encoder tube 402 and a central anti-friction sleeve 416 are interlocked by means of tangs 404 (FIG. 29d) which extend longitudinally into mating slots in the rear portion of anti-friction selleve 428.

Encoder tube 402 is supported for rotation relative to probe housing 406, in response to movements of cable 404, by central anti-friction sleeve 416 and a rearward anti-friction sleeve 440; these parts, in turn, are retained in probe housing 406 by a threaded inner bushing 444 which is turned into the rear end of housing 406 and which prevents rearward motion of an anti-friction bushing 442. Bushing 442, as can be seen in FIG. 29c, has three recesses in which fiber optic light conductors 450, 452 and 454 are seated as they spread out from cable 404 and pass into the upper and lower portions of the encoder. Central anti-friction sleeve 416 is provided with a conical surface 456 which seats on a mating, rearward-facing conical surface 485 in the central, tapering portion 459 of housing 406. By careful adjustment of threaded bushing 444, the encoder assembly held is, without binding, within probe housing 406. To this end, anti-friction sleeves 418, 416, 440 and bushing 442 are made of an anti-friction material such as the glass-filled Teflon material known as Rulon.

Fiber optic light conductors 452, 454, and 456 arrive at the probe housing in a unitary form in cable 404. To prevent undue strain on the cable from damaging the encoder assembly, cable 404 is passed into housing 406 through a screw-on tube 462 whose rear inner surface 464 contacts and retains a built-up region 466 on cable 404, acting as a strain relief. A loose fit is provided at the point of contact, so that cable 404 can rotate freely with the probe housing, while permitting the fiber optic cable and the encoder tube and encoder shaft, to turn freely with the cable as it positions itself in response to manipulation of the probe by the practitioner.

It will thus be seen that the objects set forth above, among those made apparent from the preceding description, are efficiently attained and, since certain changes may be made in the above construction without departing from the spirit and scope of the invention, it is intended that all matter contained in the above description or shown in the accompanying drawings shall be interpreted as illustrative and not in a limiting sense.

It is also to be understood that the following claims are intended to cover all of the generic and specific features of the invention herein described and all statements of the scope of the invention which, as a matter of language, might be said to fall therebetween.

What is claimed is:

1. An apparatus useful for diagnosis and treatment comprising:
    a housing means;
    actuating means disposed within the housing means and moveable therein;
    means coupled to the actuating means for providing a signal which is related to displacement of the actuating means;
    tip means removably coupled to the housing means and responsive to displacement of the actuating means to perform a function in at least one of diagnosis and treatment;
    the tip means being provided with a means for coupling the tip means to the housing means, whereupon removal the coupling means breaks causing the tip means to be inoperable after the first use.

2. The apparatus of claim 1 wherein the coupling means is destroyed when the tip means is removed from the housing means.

3. The apparatus of claim 1 wherein the housing means further comprises:
    seating means for engaging the coupling means.

4. The apparatus of claim 3 wherein the coupling means resiliently engages seating means when the tip means is placed on the housing means.

5. The apparatus of claim 4 wherein the coupling means breaks when the tip means is removed from the housing means.

6. The apparatus of claim 5 wherein the seating means comprises a coupling surface which resists decoupling of the tip means.

7. The apparatus of claim 6 wherein the tip means further comprises:
    surface means which engages the coupling surface on the housing means; and
    frangible means supporting the surface means on the tip means.

* * * * *